US009441248B2

(12) United States Patent
Laible et al.

(10) Patent No.: US 9,441,248 B2
(45) Date of Patent: Sep. 13, 2016

(54) ENGINEERED PHOTOSYNTHETIC BACTERIA, METHOD OF MANUFACTURE OF BIOFUELS

(75) Inventors: Philip D. Laible, Villa Park, IL (US); Seth W. Snyder, Lincolnwood, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 404 days.

(21) Appl. No.: 13/159,340

(22) Filed: Jun. 13, 2011

(65) Prior Publication Data

US 2011/0302830 A1      Dec. 15, 2011

Related U.S. Application Data

(60) Provisional application No. 61/354,090, filed on Jun. 11, 2010.

(51) Int. Cl.
| | |
|---|---|
| *C12N 15/82* | (2006.01) |
| *C12P 7/04* | (2006.01) |
| *C12P 5/00* | (2006.01) |
| *C12P 23/00* | (2006.01) |
| *C10L 1/02* | (2006.01) |

(52) U.S. Cl.
CPC .............. *C12P 7/04* (2013.01); *C10L 1/026* (2013.01); *C12P 5/007* (2013.01); *C12P 23/00* (2013.01); *C12Y 301/01014* (2013.01); *C10G 2300/1014* (2013.01); *C10G 2300/202* (2013.01); *C10L 2200/0469* (2013.01); *Y02E 50/13* (2013.01); *Y02P 20/52* (2015.11); *Y02P 30/20* (2015.11)

(58) Field of Classification Search
USPC ..................................................... 435/252.2
See application file for complete search history.

(56) References Cited

U.S. PATENT DOCUMENTS

| | | | | |
|---|---|---|---|---|
| 5,976,719 | A * | 11/1999 | Kim et al. .......... | 429/2 |
| 6,156,913 | A * | 12/2000 | Hyatt ............ | 549/408 |
| 6,465,216 | B2 | 10/2002 | Laible et al. | |
| 6,653,530 | B1 * | 11/2003 | Shewmaker et al. ......... | 800/282 |
| 2002/0128464 | A1* | 9/2002 | Busch et al. ............... | 536/23.6 |
| 2003/0125573 | A1* | 7/2003 | Millis et al. ................ | 549/411 |
| 2008/0319169 | A1 | 12/2008 | Firestone et al. | |
| 2011/0256594 | A1* | 10/2011 | Cranford et al. ............ | 435/134 |

OTHER PUBLICATIONS

Takeda et al., Geranylgeraniol, an Intermediate Product in Mevalonate Pathway, Induces Apoptotic Cell Death in Human Hepatoma Cells: Death Receptor-independent Activation of Caspase-8 with Down-regulation of Bcl-xL Expression, 92 Jpn. J.Cancer Res., 918-925 (2001).*
Shcolnick et al., Metal Homeostasis in Cyanobacteria and Chloroplasts. Balancing Benefits and Risks to the Photosynthetic Apparatus, 141 Plant Physiology, 805-810 at 805 (2006)).*
Valentin et al. (The Arabidopsis vitamin E pathway gene5-1 Mutant Reveals a Critical Role for Phytol Kinase in Seed Tocopherol Biosynthesis, 18 Plant Cell, 212-224 at 213, Figure 1 (2006)).*
Misawa et al. (Expression of a tomato cDNA coding for Phytoene Synthase in *Escherichia coli*, Phytoene Formation In Vivo and In Vitro, and Functional Analysis of the Various Truncated Gene Products, 116 J Biochem., 980-985 (1994)).*
Arkus et al. (Development of a high-throughput purification method and a continuous assay system for chlroophyllase, 353 Analytical Biochemistry, 93-98 (2006)).*
Young (Bacteriophage Lysis: Mechanism and Regulation, 56 Microbiological Reviews No. 3, 430-481 (1992)).*
Pongprayoon et al. (Antispasmodic Activity of β-Damascenone and E-phytol Isolated from Ipomoea pes-caprae, 58 Planta Med., 19-21 (1992)).*
Rojas-Duran et al, 2009, Caribbean Journal of Sci., 45:118-124.*
Chew et al, 2007, Annu. Rev. MicroBiol., 61:113-129.*
Laible et al, 2008, Foreign Gene Expression in Photosynthetic Bacteria, Springer-Verlag, New York, p. 1-22.*
Tavano et al, 2006, Curr. Op. Microbiology, 9:625-631.*
Taguchi A., et al., Biochemical characterization and electron-transfer reaction of syml, a Rhodobacter capsulatus symmetry mutant which affects the initial electron donor, Biochemistry, 1992, 31: pp. 10355-10355.
Drahl, C., Retooling A Bacterial Biofuel Factory, Chemical & Engineering News, published by The American Chemical Society, Apr. 11, 2011, pp. 36-37.
Theiler R., et al., Complete Amino Acid Sequence of the B875 Light-Harvesting Protein of Rhodopseudomonas Sphaeroides Strain 2.4.1: Comparison with R26.1 Carotenoidless-Mutant Strain, FEBS Letters 1985; 184 (2): pp. 231-236.
Murphy, M., et al., Compendium of Experimental Cetane Number Data, Subcontractor Report, National Renewable Energy Laboratory, Golden, Colorado, Sep. 2004.
Laible, P., et al., Foreign Gene Expression in Photosynthetic Bacteria, The Purple Phototrophic Bacteria, Springer-Verlag, New York, 2008.
Laible, P., el al., Membrane Protein Production in Rhodobacter: a Practical Guide, Weinheim: Wiley-VCH, 2011.
Dang, H., et al. Numerical Dominance and Phylotype Diversity of Marine *Rhodobacter* Species during Early Colonization of Submerged Surfaces in Coastal Marine Waters as Determined by 16S Ribosomal DNA Sequence Analysis and Fluorescence In Situ Hybridization, Applied and Environmental Microbiology, 2002, 68(2): pp. 496-504.
Tanaka, R., et al., Reduced Activity of Geranylgeranyl Reductase Leads to Loss of Chlorophyll and Tocopherol and to Partially Gerany.lgeranylated Chlorophyll in Transgenic Tobacco Plants Expressing Antisense RNA for Geranylgeranyl Reductase, Plant Physiology, Jul. 1999, 120: pp. 695-704.

(Continued)

*Primary Examiner* — Jason Deveau Rosen
(74) *Attorney, Agent, or Firm* — Cherskov Flaynir & Gurda, LLC

(57) ABSTRACT

The invention provides for a novel type of biofuel; a method for cleaving anchors from photosynthetic organisms; and a method for producing biofuels using photosynthetic organisms, the method comprising identifying photosynthesis co-factors and their anchors in the organisms; modifying the organisms to increase production of the anchors; accumulating biomass of the organisms in growth media; and harvesting the anchors.

19 Claims, 20 Drawing Sheets

(56) References Cited

OTHER PUBLICATIONS

Arkus, K., et al., Mechanistic Analysis of Wheat Chlorophyllase. Archives of Biochemistry and Biophysics, 2005, 438: pp. 146-155.
Abeliovich, A., et al., Bacteriophages of Rhodopseudomonas spheroides: Isolation and Characterization of a Rhodopseudomonas spheroides Bacteriophage, Journal of Virology, 1974: 13(6), pp. 1392-1399.
Simon, R., et al., A broad host range mobilization system for in vivo genetic engineering: Transposon mutagenesis in gram negative bacteria. Bio/Technology, 1983, 1, pp. 37-45, 784-791.
Hossain Abms, et al., Biodiesel Fuel Production from Algae as Renewable Energy, American Journal of Biochemistry and Biotechnology, 2008, 4: pp. 250-254.
Jacob-Wilk, D., et al., Chlorophyll breakdown by chlorophyllase: isolation and functional expression of the Chlase1 gene from ethylene-treated Citrus fruit and its regulation during development, The Plant Journal, 1999, 20: pp. 653-661.
Laible, P., et al., Towards higher-throughput membrane protein production for structural genomics initiatives, Journal of Structural and Functional Genomics, 2004, 5: pp. 167-172.
Mackenzie, C. et al., Postgenomic Adventures with Rhodobacter sphaeroides, Annual Review of Microbiology, 2007, 61: pp. 283-307.
Pokkuluri, P., et al., The structure of a mutant photosynthetic reaction center shows unexpected changes in main chain orientations and quinone position, Biochemistry, 2002, 41(19): pp. 5998-6007.
Porter, S., et al., Rhodobacter sphaeroides: complexity in chemotactic signaling, Trends in Microbiology, 2008, 16: pp. 251-260.
Puskas, A., et al., A Quorum-Sensing System in the Free-Living Photosynthetic Bacterium *Rhodobacter sphaeroides*, Journal of Bacteriology, 1997, 179: pp. 7530-7537.
Senge, O., et al., Biosynthesis and Structures of the Bacteriochlorophylls, Anoxygenic Photosynthetic Bacteria, Kluwer Academic Publishers, Dordrecht, pp. 137-151.
Som, S., et al., Nozzle Flow Characterization of Alternate Fuels for Compression Ignition Engine Applications, presented at SAE 2011 World Congress, Detroit, Michigan, Apr. 12, 2011.
Keller, Y., et al., Metabolic compartmentation of plastid prenyllipid biosynthesis: Evidence for the involvement of a multifunctional geranylgeranyl reductase, Eur. J. Biochem., 1998, 251: pp. 413-417.
Oelze J., Methods in Microbiology, vol. 18, Gerthard Gottschalk, Academics Press, London, 1985, pp. 257-282.
Feher G., et al., The Photosynthetic Bacteria, New York, Plenum Press, 1978, Chapter 19, pp. 349-386.

* cited by examiner

At = *Arabidopsis thaliana*; soy = soybean; Gb = *Ginkgo biloba*; corn = corn; (f) = field; and (BC) = BioChain.

A. phytol control
B. negative control (0)
C. Arabidopsis thaliana (7324)
D. Brassica oleracea (9649)
E. Zea mays (corn; 11729)

A. phytol standard  B. ΔbchGΔispA
C. ΔbchG  D. ΔbchGΔcrtBΔispA
E. ΔcrtBΔbchG  F. R26[pRKGbChlHT1Dpuf]
G. ΔcrtB[pRKGbChlHT1Dpuf]

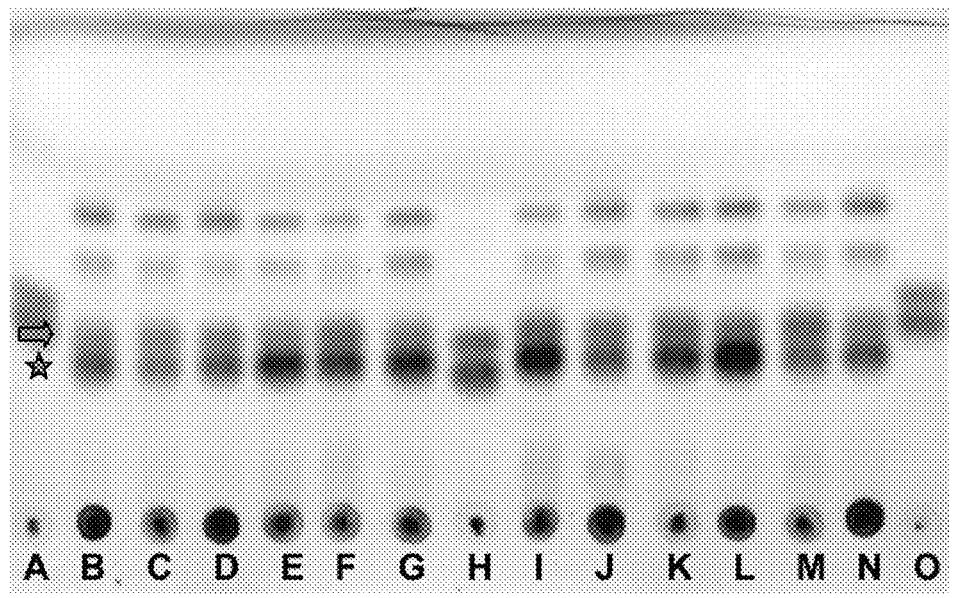

A. phytol standard (chemically pure but isomeric mixture)
B. 2.4.1[pRKBioChGmChl3HT1Dpuf]
C. R26[pRKBioChGmChl3HT1Dpuf]
D. 2.4.1[pRKfGmChl3HT1Dpuf]
E. R26[pRKB73ZmChl2HT1Dpuf]
F. ΔcrtB[pRKAtChl2HT1Dpuf]
G. R26[pRKAtChl1HT1Dpuf]
H. farnesol standard (chemically pure but isomeric mixture)
I. ΔcrtB[pRKB73ZmChl2HT1Dpuf]
J. 2.4.1[pRKBoChl1HT1Dpuf]
K. ΔcrtB[pRKAtChl1HT1Dpuf]
L. 2.4.1[pRKB73ZmChl2HT1Dpuf]
M. ΔcrtB[pRKBioChGmChl3HT1Dpuf]
N. ΔcrtB[pRKfGmChl3HT1Dpuf]
O. phytol standard (chemically pure but isomeric mixture)

FIG. 12

A. phytol standard  B. whole cells
C. membranes  D. cell debris pellet
E. spent media A. phytol standard
B. *Ginkgo biloba* (7896)
C. *Brassica oleracea* (14706)
D. *A. thaliana* (63873)
E. corn (80294)
F. field soybean (79279)

A1. phytol standard
A2. R26[pRKB73ZmClh2HT1Dpuf]
A3. geranylgeraniol
B1. phytol standard
B2. *in vitro* phytol control
B3. ΔcrtB[PRKfGmClh3HT1Dpuf]
B4. ΔcrtB
B5. farnesol standard
B6. black cellular residue
B7. geranylgeraniol standard ical Application No. 61/354,090 filed on Jun. 11, 2010,
ENGINEERED PHOTOSYNTHETIC BACTERIA, METHOD OF MANUFACTURE OF BIOFUELS

PRIORITY

This Utility Application claims the benefits of U.S. Provisional Application No. 61/354,090 filed on Jun. 11, 2010, the entirety of which is incorporated herein by reference.

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

BACKGROUND OF THE INVENTION

1. Field of the Invention

This invention relates to a method for producing biofuels, and more specifically this invention is related to utilizing naturally occurring biological pathways, both photosynthetic and non-photosynthetic, as a method for manufacturing biofuels.

2. Background of the Invention

Rising energy prices, supply uncertainties, and environmental concerns all threaten the security of the United States. Production of fuel from renewable energy sources, more particularly from agricultural sources, provides a way to enhance the nation's security. Also, the search continues for ways to produce biofuels without competing with land use for food, high-yield farmlands, or increasingly limited water resources.

Currently, ethanol is the primary biofuel, produced primarily from grain or sugar cane. There are significant development efforts to produce ethanol from cellulosic materials.

Biodiesel, produced by a transesterification of vegetable oil, is the second largest biofuel. Biodiesel is not an ideal fuel because its long chain length ester linkages affect combustion properties enough that it does not serve as a direct replacement for petroleum diesel. Biodiesel is primarily produced from edible oil seeds including soybeans, canola (rapeseed), or tropical oils such as palm. There are significant efforts to produce biodiesel from non-competitive oil seeds, including jatropha and pennycress.

Recently there has been significant research interest to produce biodiesel from aquatic species, primarily microalgae. Production of biodiesel from microalgae would address competition regarding land and resource use in comparison to edible oil seeds. Transition to algae-based biodiesel does not address the compatibilities issues regarding biodiesel.

Several factors have contributed to the lack of monumental breakthroughs in the biofuels field. Among them include the fact that teams are working to make fuels that directly mimic gasoline and diesel. For example, many investigators are employing chemical reduction of traditional triglycerides or fatty acids. These strategies require both chemical reactors and sources of hydrogen or other reducing molecules. With current technology, the hydrogen must be derived from fossil fuel or biomass gasification.

Production of fuel-like molecules in eukaryotes is challenging. Higher plants and algae are relatively complex organisms and so are genetic engineering efforts to manipulate them. In addition, higher plants and algae are less flexible in their ability to adapt and thrive in a variety of growth conditions and environments, and, hence, are more expensive to cultivate.

A need exists in the art for a method to produce fuel-like molecules from organisms with a minimum number of genetic modifications to the organisms. Any biofuel system and method for producing biofuel should not compete with food production resources, such as high-yield farmland.

SUMMARY OF INVENTION

An object of the invention is to provide a method to engineer photosynthetic bacteria to produce biofuels, infrastructure compatible or new fuels, which overcomes many of the disadvantages of the prior art.

Another object of the invention is providing a method for the production of biofuels or biofuel precursor molecules from novel feedstocks using organisms that have not yet been harnessed for this purpose. A feature of the invention is the use of a combination of engineered and natural photosynthetic mechanisms to generate fuel or fuel-precursor molecules. An advantage of the invention is that the organisms are easily engineered to over-produce the desired molecules. Another advantage is that the organisms naturally, or with minor alteration, export these molecules from the cell to a growth medium, thereby simplifying the harvesting of the target molecules.

Still another object of the present invention is to provide a system utilizing engineered photosynthetic bacteria to facilitate production of biofuels and biofuel precursors. A feature of the invention is that the system approximates carbon neutrality inasmuch as the majority of carbon embodied as biomass is fixed by the cells that are also producing the fuel. An advantage of the invention is that the system produces biofuels with or without fermentation or distillation, therefore making it more flexible from an energy use and efficiency perspective compared to state-of-the-art biofuels production processes. Another advantage is that the resulting moieties need not undergo further refining before blending with existing fuels, or consumed directly.

Yet another object of the present invention is to provide a biological-based, noncompeting system to produce biofuels. A feature of the invention is the use of a resource which is not used for any other major activity, such as food production. An advantage of the invention is that its prokaryotic foundation makes it easy to engineer, grow and utilize.

Another object of the present invention is to provide a natural, cost and energy efficient mechanism to extract the desired biofuel molecules from the growing cells and/or medium in which photosynthetic organisms are cultured. A feature of the invention is that photosynthetic bacteria possess natural machinery which excretes target biofuel molecules into the medium, thereby providing a simple method of harvesting target biofuel molecules from the culture medium by either separation through a natural density gradient or by centrifugation. For example, the method enables the generation of target moieties and/or their encapsulating structures which have densities different than the densities of the growth medium.

Still another object of the present invention is to facilitate an efficient and uncomplicated collection process of desired biofuel molecules from growth media. A feature of the invention is that cells that have sequestered or otherwise encapsulated the target hydrocarbons are buoyant and will float to the surface of the medium. An advantage is that the foregoing cells can be collected via negative pressure, (i.e., by vacuuming or suction), centrifugation, skimming, or otherwise harvesting the cells from the surface of the medium, inasmuch as the cells will float to the surface of the medium.

Yet another object of the present invention is to generate fewer waste products. A feature of the invention is its "value-added" attribute in producing usable "waste." An advantage of the invention is that its "waste" products consist of between 30 to 70 percent lipids that can be used to produce other fuel sources.

Briefly, the invention provides a method for producing biofuels using photosynthetic organisms, the method comprising identifying photosynthesis co-factors and their anchors in the bacteria; modifying the bacteria to increase production of the anchors; accumulating biomass of the bacteria in growth media; and harvesting the anchors. A myriad of organisms are suitable, including those grown anaerobically, semi-aerobically, aerobically, heterotrophically, using sugars as their carbon and energy source, using alcohol and acetone as their carbon and energy source, and using radiation, such as visible light.

Also provided is a method for harvesting fuel-precursor moieties from biological systems. A feature of the method is using an enzyme, for example Chlorophyllase, to cleave anchoring domains from photosynthetic bacterial molecules.

Furthermore, the invention provides for a biofuel comprising moieties between about 5 and 30 carbons in length wherein the moieties are generated from interruptions of biosynthetic pathways of photosynthetic bacteria. The biofuels have lipids as a by-product. The biofuel has moieties of a carbon to oxygen weight ratio of between approximately 1:0 and 10:2.

These and other features and advantages of the biofuel and its production of the present disclosure will become more apparent to those ordinarily skilled in the art after reading the following Detailed Description of the Invention and Claims in light of the accompanying drawing Figures.

BRIEF DESCRIPTION OF DRAWING

The invention together with the above and other objects and advantages will be best understood from the following detailed description of the preferred embodiment of the invention shown in the accompanying drawings, wherein:

FIG. 12 is a stained chromatographic plate showing phytol levels produced from neofunctionalized strains;

DETAILED DESCRIPTION OF THE INVENTION

Figure 1:
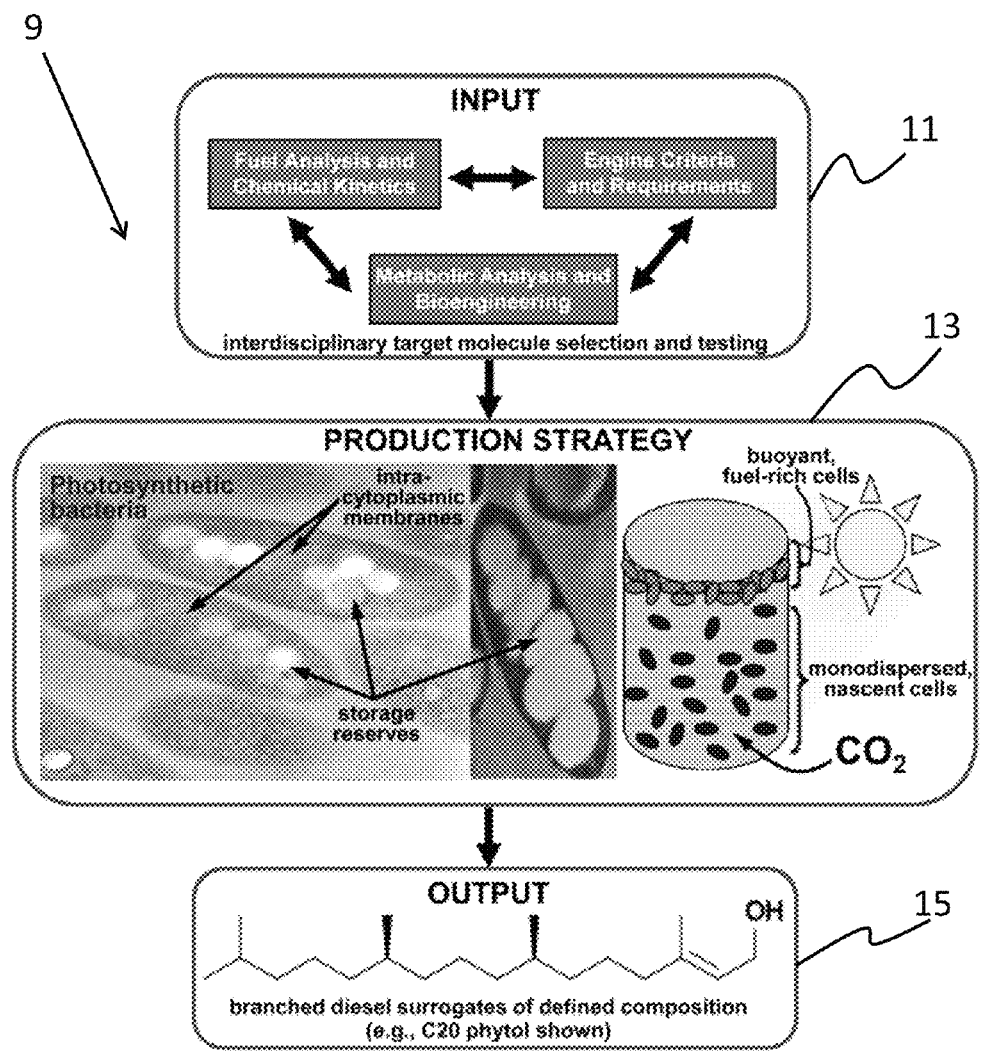
FIG. 1 is a schematic depiction of the overall approach including the invented method for production of co-factors and anchors as bio fuel precursors, in accordance with features of the present invention.

The foregoing summary, as well as the following detailed description of certain embodiments of the present invention, will be better understood when read in conjunction with the appended drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention enables the production of "drop in" fuels and fuel precursors, i.e., those moieties that state of the art combustion systems are engineered to utilize. The invention also enables the production of intermediate moieties for use in the production of petroleum-based products, such as plastics, synthetics, composites, insecticides, paints, medicine, etc.

The invention embodies the salient features of bio-engineered fuels, those features including the following:

- Fuels, fuel precursors and fuel intermediates are generated from renewable sources/feedstocks;
- Engineering of a known bacteria assures relatively easy manufacturing, growing and cultivating of the bacterial and resulting product;
- Target moieties are produced in a manner where the end product can be further engineered or modified easily such that output can be tailored to meet varied and specific needs;
- Target moieties are manufactured from material that limits resources needed for production;
- Use of bacteria results in minimal use of resources such as time, land and water;
- Produced fuel uses a source that avoids competition with other human and environmental activities (e.g. food and feed production);
- Any fuel moieties produced are extracted such that harvesting/refining complexities, and therefore costs, are minimized;
- The invented process significantly reduces greenhouse gas emissions on a life cycle basis;
- Resulting fuel produced permits and promotes efficient combustion; and
- Resulting fuel produced does not require significant changes in the infrastructure for producing, distributing, or utilizing the fuel.

The invention provides a biologically based method for producing specific carbon length fuel molecules or fuel precursors, where the carbon length is selected as a replacement for gasoline, diesel, jet fuel, and a combination of these fuels. Furthermore, the method controls branching of the target molecule so as to optimize combustion and minimize soot formation. Also, the method generates fuel precursor moieties, such as phytol, with relatively less oxygen (5 percent) compared to fuels such as ethanol (35 percent) and transesterified biodiesel (12 percent) produced by other biofuel production methods. The invented method also controls the degree of saturation/unsaturation of the targeted moieties. Therefore, the present method generates fuels having oxygen content by weight that is less than half the weight of moieties produced by state-of-the-art biosystems.

The present invention relates to the engineering and leverage of prokaryotes, such as photosynthetic bacteria, for the production of biofuels and biofuel precursors. In an embodiment of the invention, photosynthetic bacteria are engineered to store excess energy in internal, compartmentalized reserves in the form of polymers, which makes them flocculent. These flocculents are harnessed to produce, concentrate, store, and release large amounts of engineered molecules with similar properties. Photosynthetic bacteria are discussed herein to illustrate the utility of the invented method. However, any photosynthetic organism, including algae, can be used to work the invention.

Preferred organisms for incorporating into the invented method are members of microbial communities. This assures that the organisms possess mechanisms to export different metabolites from their interiors and into regions exterior to the cell, such as growth media. This provides a means for the bacteria to share resources and acquire necessary intermediates from other members of the community.

Embodiments of the present invention use engineered or un-engineered pathways, to export fuel or fuel-precursor molecules from cells. This export capability will likely limit the stress or 'sickness' imposed to the organism from overproduction of certain substrates, be those substrates native or non-native. This is also a key advantage to the use of bacteria in biofuel production in that the harvesting metabolites will be more cost effective as separation processes are simplified. With no costly (monetarily and environmentally) chemical processing required, these approaches allow for efficient synthesis of biofuels, limiting or excluding post-separations steps.

Photosynthetic Bacteria Detail

Photosynthetic bacteria flourish in a multitude of growth regimes (e.g., photosynthetic, chemoheterotrophic), grow in the presence and absence of oxygen (being facultative anaerobes), and utilize a diverse selection of carbon sources. They are unicellular and readily transport molecules in and out of living cells. In wild (unengineered) organisms, their photosynthetic machinery often comprises a significant portion of total cell mass. This photosynthetic machinery is highly pigmented and includes cofactors (chlorophyll, carotenoids, quinones, etc.) that are positioned properly within proteins by long hydrocarbon tails which serve as co-factor anchoring domains. These anchoring domains associated with their respective photosynthetic co-factor molecules provide template feedstocks for the fuels (drop-in or new) generated by the engineered prokaryotes.

An embodiment of the invented method involves modification of biochemical pathways involved in synthesis of these essential cofactors. Specifically, these cofactors are synthesized in excess when biosynthetic pathways for their production are interrupted by: the removal of genes (producing deletion strains or "knock-out" mutants), modification of regulatory mechanisms to produce extra amounts of naturally-exhibited enzymes (generating overproducing strains), or addition of new enzymatic activities by introducing genes from other species (creating 'neofunctionalized' strains).

Along with excess production of co-factors comes excess production of their anchoring domains. Such anchor molecules are chemically more related to potential fuel molecules than fatty acids. Ideal fuel molecules are chemically reduced, i.e. have low oxygen content, and have fewer unsaturated carbons than naturally produced molecules of similar carbon length. In addition, ideal fuel molecules have carbon chains of between about 5 and 20 carbons which is a range suitable for combustion (i.e. similar to gasoline, diesel, or jet fuel) and have a moderate amount of carbon branching to act as initiation points for combustion. Similarly, the aforementioned anchoring molecules have carbon chain lengths of between approximately 5 and 20.

A salient feature of this invention is the overproduction of photosynthetic co-factors and their anchoring molecules. The extent of production of the co-factors and their anchors are monitored using visible radiation, UV radiation, buoyant density, and combinations thereof. Cofactors and their long chain anchoring moieties comprise between 20 and 90 percent of photosynthetic functional units in photosynthetic bacteria when the cells are grown anaerobically with light. The cofactors catalyze ultrafast charge-separation reactions that occur with extreme efficiency. The efficiency is brought about by careful placement (via their anchors) of the cofactors within protein matrices. The cofactor placement where distances and orientational relationships are ultra-critical is dictated in large part by their anchors, which are long hydrocarbon tails that interact with proteins and lipids in the membrane bilayer.

An embodiment of the invention is a method for partially interrupting the biosynthetic pathways of these cofactors and engineering these organisms to overproduce grossly and to export efficiently the long hydrocarbon tails (and/or derivatives thereof), comprising the anchors, into the growth medium. Therefore, the solar-driven photosynthetic energy that they utilize for growth (250-1000 nm; mainly far-UV 300-450 nm and near-IR 700-900 for photosynthetic bacteria and 350-750 nm for algae) will be harnessed to produce fuel molecules or precursors which will not require further refining such as extensive chemical or biochemical conversion.

Some specific examples of biofuels produced using this approach include truncated forms of phytol, isoprenols (alcohols made from repeating isoprenyl units), and atypical alcohols using carotenes as the starting point.

FIG. 1 is a schematic depiction illustrating a general overview of the approach, that overview designated as numeral 9.

First, target molecules are selected and tested at the input stage 11. Selection and testing of target molecules is based on infrastructure compatibility, fuel chemical composition, fuel metabolic characteristics, and bioengineering processes involved.

Once the target molecule is selected, a production process 13 is initiated, comprising accumulation of biomass, and subsequently unrefined target moiety. The output 15 yield comprises the product (i.e. target molecule). In addition, approximately 25 to 70 weight percent of material generated by the invented process is "waste" comprising lipids. The generated lipids in this waste can be processed into traditional lipid-based biofuels. Therefore, the invented method creates "value-added" products, inasmuch as its secondary streams are feedstocks for fuel precursors as well. In an embodiment of the invention, about 30 to 70 weight percent of the secondary waste streams comprises lipid when algae is used to generate target molecules.

*Rhodobacter* species can be induced to produce target biofuel molecules along with large amounts of lipids; typically between 25 to 30 weight percent of the resulting waste product can be attributed to lipids. Here, the media and broken cells will include lipids produced by the organisms.

The lipids can be converted to traditional biodiesel using transesterification processes known in the chemical art. In a similar application, lipid transesterification is seen as the method to produce biofuels from algae.

A second use of the residuals is to convert any excess or excreted sugars remaining in the media into either ethanol or biobased chemicals, by known pretreatment or fermentation methods. A third use of the residuals is to treat the residuals by anaerobic digestion to produce methane. Such anaerobic digestion processes are known to practitioners.

Co-factor anchoring molecules comprising hydrocarbon chains are extracted from the medium and used as fuels or fuel precursors. Simultaneous export of these molecules from the organism is not required for the realization of the value of these engineered strains, but it does provide a means for facilitating harvesting of the fuel moieties from the media without destruction of the originating biomass. In certain instances, simultaneous export of anchoring moieties may not be desired, inasmuch as storage vacuoles within a cell that are swollen with the desired molecular anchors cause the cell to become buoyant, compared to the remaining constituents of the growth liquor. This buoyancy provides a means for separating the lower density cells containing the target biofuel molecules from the higher density broth (and 'immature cells') to facilitate harvesting of the target molecules.

A myriad of photosynthetic organisms are suitable biofuel processors in the invented method, including, but not limited to the following genera of photosynthetic bacteria:

Green Sulfur Bacteria
*Chlorobium*
*Prosthecochloris*
*Ancalochloris*
*Pelodictyon*
*Chloroherpeton*
Purple and Green Bacteria
*Thiospirillum*
*Thiorhodovibrio*
*Blastochloris*
*Chromatium*
*Thiocystis*
*Lamprocystis*
*Lamprobacter*
*Thiodictyon*
*Amoebobacter*
*Thiopedia*
*Thiocapsa*
*Ectothiorhodospira*
*Rhodosprillum*
*Rhodopila*
*Rhodomicrobium*
*Rhodobacter*
*Rhodopseudomonas*
*Rhodocyclus*
*Rhodoferax*
*Rubrivivax*
*Heliobacter*
*Heliobacter*
Filamentous Anoxygenic Phototrophs
*Chloroflexus*
Marine *Chloroflexus*-like organisms
*Heliothrix*
*Chloronema*
*Oscillochloris*
Aerobic Anoxygenic Phototrophs
*Eythrobacter*
*Roseobacter*
*Methylobacterium*
*Porphyrobacter*
*Rhizobium*
*Acidiphilium*
*Erythromicrobium*
*Roseococcus*

The invented process also works if these organisms are grown non-photosynthetically, i.e., where the energy is provided by carbon molecules such as sugars or acetone or by chemical or electrochemical reducing equivalents. In addition, if these metabolic pathways are incorporated in non-photosynthetic organisms, they will produce the targeted fuel molecules using energy provided by carbon molecules or their reducing equivalents.

For the sake of illustration, a portion of this specification will deal with one embodiment of the invention, which uses photosynthetic bacteria, specifically non-sulfur, purple bacteria. The advantage of using this organism is that it can be easily engineered to synthesize long-chain hydrocarbons while simultaneously storing/sequestering them in large intracellular membrane systems. These bacteria also enable export of fuel moieties and their precursors into growth media for ease of processing.

While non-sulfur, purple bacteria are used for illustrative purposes herein, the invented engineering protocol can be applied to other bacteria as well as to algae to obtain similar results. This is due to photosynthetic bacteria and algae all having specific regions in their respective genomes dedicated to co-factor and co-factor anchor production.

Figure 2:
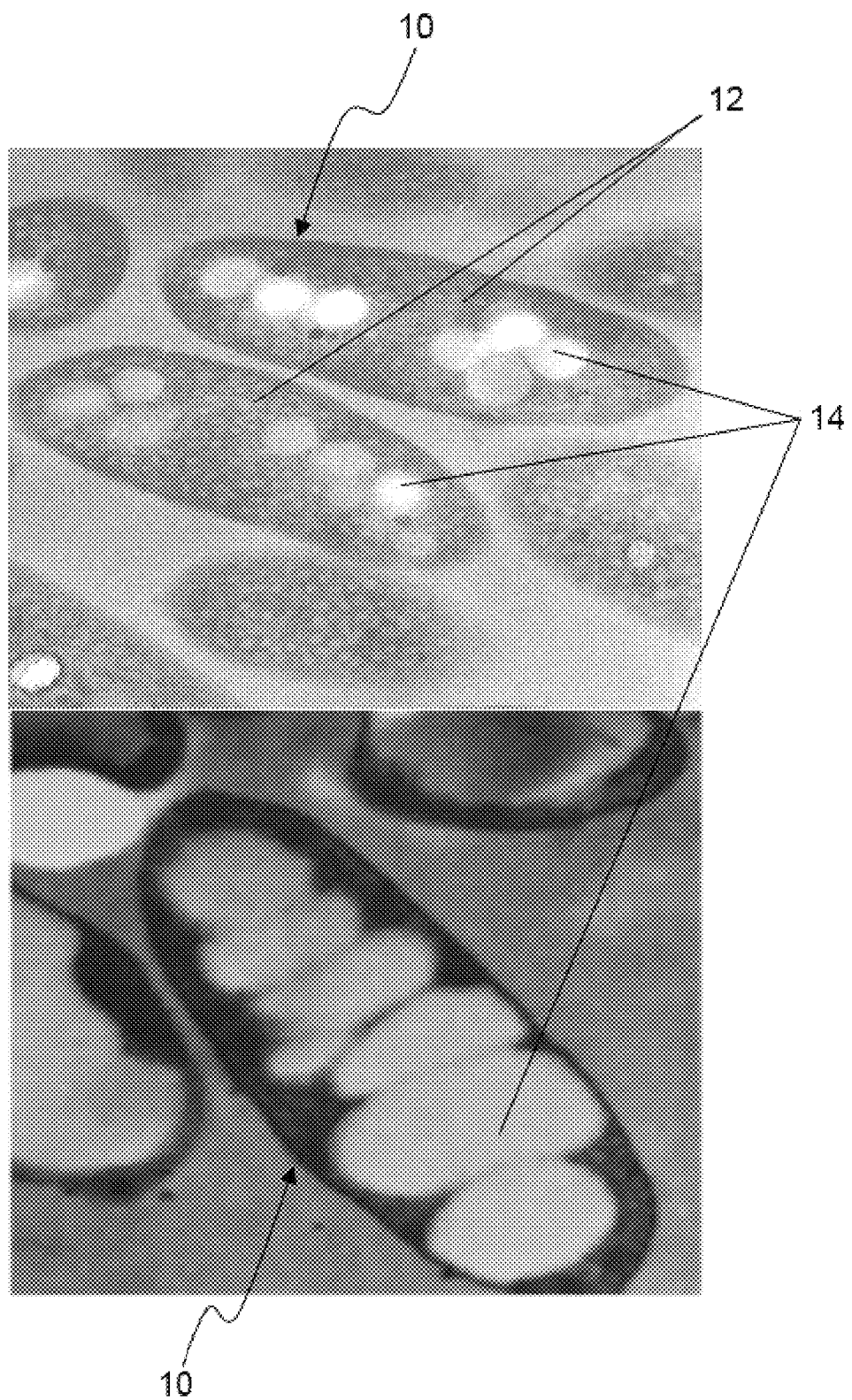
FIG. 2 is an electron micrograph of photosynthetic bacteria showing intracytoplasmic membranes and storage vesicles.

FIG. 2 is an electron micrograph of exemplary bacteria 10, the micrograph depicting intra-cytoplasmic membranes 12, and storage reserves 14.

One advantage of using Rhodobactor in this system is the large number of invaginations of the inner cell membrane that elaborate extensively when the cells are using photosynthetic growth modes or are anticipating a switch to photosynthetic growth modes in the near future. These membrane invaginations are the intracytoplasmic membranes, 12, which house the protein machinery and cofactors—with long hydrophobic tails—that are used to harvest sunlight and convert it into useful biological equivalents.

A second feature to note in FIG. 2 is that, in an embodiment of the invented system, the contents of large storage reserves, 14, comprise almost exclusively short-chain hydrocarbons such as poly-beta-hydroxybutyrate, which are used as energy storage molecules for growth at night, when stimulating radiation is not present, or when the environment turns unfavorable for other growth regimes. If storage reserves become large enough (such that the vesicles swell to volumes that approach a significant fraction of the entire volume of the cell; generally at least 50 percent of the cell volume, preferably at least 60 percent, and most preferably at least 75 percent of the entire cell volume), the cells are buoyant relative to surrounding growth media. This feature translates to cells that are difficult to pellet via centrifugation using normal conditions 10,000×g), and therefore float on the surface. But this feature provides a means for separating still viable cells as a less dense phase from the more dense broth. These storage reserves also provide a means for storing concentrated levels of the target moieties.

These bacteria grow photosynthetically on simple, rich, and/or defined media, and are unicellular; thus, they are relatively easy to genetically engineer. They represent metabolically diverse genera and therefore utilize a variety of growth modes, depending on the production strategy chosen. Other photosynthetic organisms, such as algae, also can be used.

Figure 3:
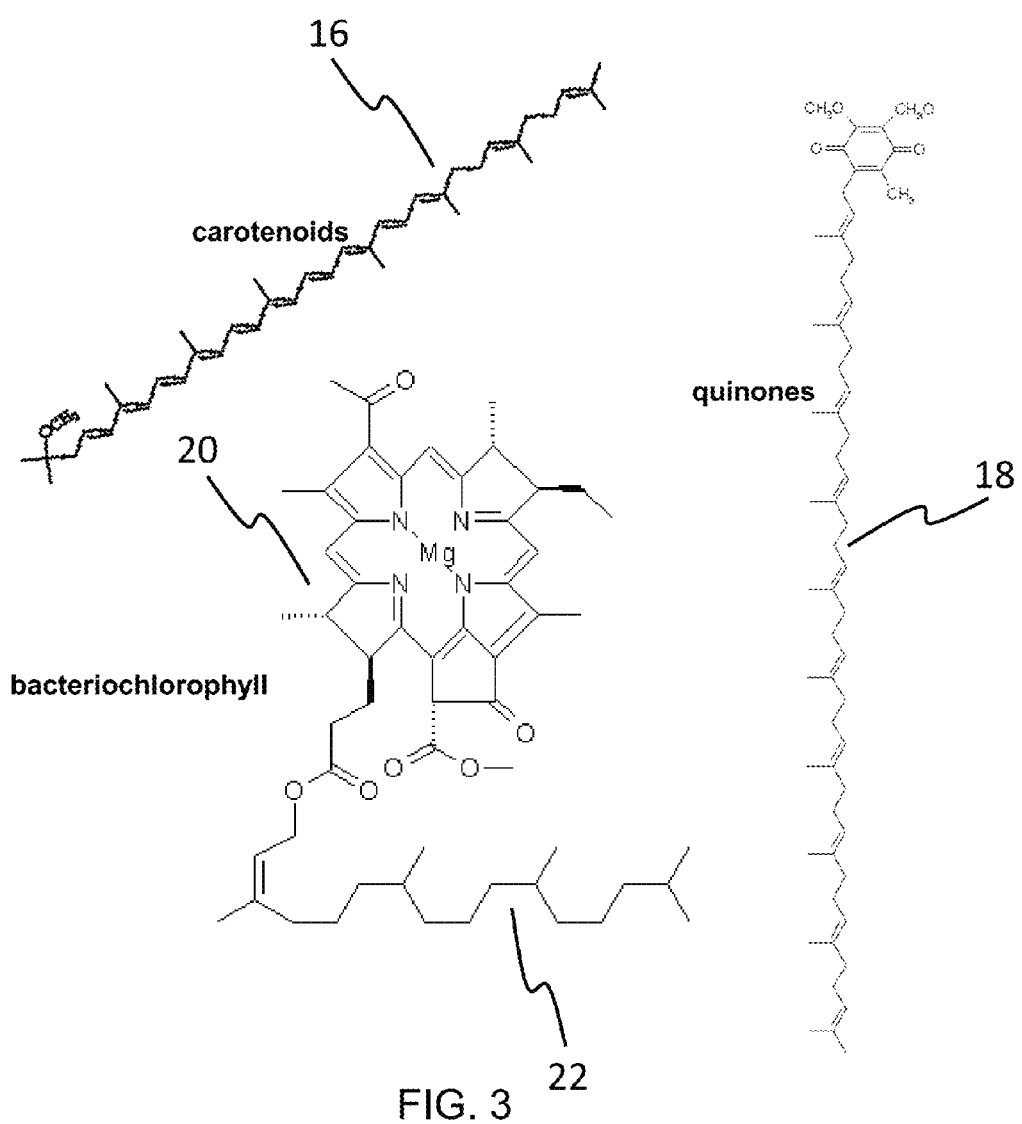
FIG. 3 are chemical structures of co-factors found in photosynthetic bacteria.

The bacteria produce large amounts of cofactors comprising long, hydrocarbon tails. Exemplary cofactors are depicted in FIG. 3, and include carotenoids 16, quinones 18, and bacteriochlorophyll 20. The cofactors, and therefore the anchors, comprise a significant fraction of the final cell weight.

The cofactors are anchored in membrane proteins by long hydrocarbon tails, comprised of 15 or more carbon molecules. Some of the co-factors are unsaturated (multiple carbon-carbon double bonds), like carotenoids and quinones, while some of the anchoring moieties are more reduced, like the phytyl tail of bacteriochlorophyll. These differences impact the fuel-like properties of the biological molecules. All the cofactors exhibit branching, and branching promotes efficient combustion and reduces soot formation.

Bacteria suitable for use in the invented method are biofilm forming organisms naturally endowed (or engineered) with the ability to export many types of products outside the cell. An embodiment of the invented method is the engineering of different groups of transporters which move hydrophobic molecules across membranes. For example, there are at least three major groups of ABC transporters. These proteins are best known for their ability to confer multidrug resistance. In addition, ABC transporters comprise significant targets of therapeutic interventions in medicine, including cancer drug resistance, lipid and other metabolic disorders, and even gene therapy applications. Expression of these genes can be upregulated in production strains or new genes from other organisms so as to enable the transport of target fuel molecules to different regions of the interior of the cell or to regions exterior of the cell. For example, this engineering might result in more efficient export of target molecules being manufactured within the cell, and the export of potentially toxic materials from the cell, thereby providing a means to both export fuel molecules while maintaining the viability of the biomass for continued fuel moiety production.

Rhodobacter

Certain *Rhodobacter* bacteria provide specific advantages for producing biofuels because they produce large amounts of membrane-localized pigments under specific growth conditions in response to environmental cues, such as light intensity and/or oxygen tension. Suitable members of this *Rhodobacter* genus are facultative photoheterotrophs characterized by a metabolic diversity that allows them to adapt readily to a wide variety of environmental conditions. They are known to reduce nitrogen compounds, fix carbon dioxide, utilize carbon sources in an aerobic environment, grow photosynthetically under anaerobic conditions, or grow anaerobically in the dark in the presence of exogenous electron acceptors. Also, *Rhodobacter* is lithotrophic, which is to say that it can use inorganic electron donors to facilitate electron transport. Exemplary *Rhodobacter* species include *Rhodobacter adriaticus, Rhodobacter aestuarii Venkata, Rhodobacter blasticus, Rhodobacter capsulatus, Rhodobacter changlensis, Rhodobacter euryhalinus, Rhodobacter indicus, Rhodobacter johrii, Rhodobacter megalophilus, Rhodobacter sphaeroides, Rhodobacter sulfidophilus, Rhodobacter veldkampii, Rhodobacter vinaykumarii.*

Members of the *Rhodobacter (R.)* genus are versatile organisms that may be cultured to high cell densities in the presence or absence of light (without or with oxygen, respectively) on a variety of rich or defined minimal media, disclosed supra.

Under conditions of low levels of incident radiation (light-harvesting arrays in photosynthetic bacteria can utilize UV, visible, and near IR wavelengths) and/or lowered oxygen tension, the *Rhodobacter* membrane surface increases many-fold to emerge as an intracytoplasmic membrane (ICM; noted as item 12 in FIG. 2). In essence, the ICM is the result of invaginations of the cytoplasmic membrane. This inducible ICM of *Rhodobacter* has been exploited for the expression of foreign membrane proteins, as described in U.S. patent application Ser. No. 12/148,518, which is incorporated herein by reference. Concomitantly, the same environmental cues, which produce the ICM, induce synthesis of the photosynthetic apparatus—the peripheral (LHII) and core (LHI) light-harvesting assemblies and the reaction center (RC). The new ICM sequesters these complexes that are composed of transmembrane polypeptides and their associated hydrophobic redox and energy transfer cofactors with hydrocarbon tails (one such tail is boxed and depicted in FIG. 4). As noted supra, these tails anchor the co-factors to the membrane.

Fuel Molecule Targets

In consideration of the combustion properties of fuel molecules, the inventors have identified several fuel molecules that can be produced using the invented system. These fuel molecules include phytol and geranylgeraniol, and variously reduced forms of the latter. Some of the molecules also serve as intermediates for methods not related to fuel production. Some of the molecules may be precursors that require thermochemical or catalytic modification after biological production.

Preferable target biofuels have the least number of carbon double bonds. Suitable biofuel feedstock candidates include moieties having between approximately 5 and 70 carbons, preferably between 5 and 20, and most preferably between 5 and 15 carbons. For example, the primary targets of an embodiment of the invention are the C5-, C10-, and C15-precursors involved in the synthesis of phytol (a branched C20 alcohol). The five-carbon length isopentenyl pyrophosphate (IPP) intermediate serves as the template for synthesizing each of these precursors.

Figure 5:
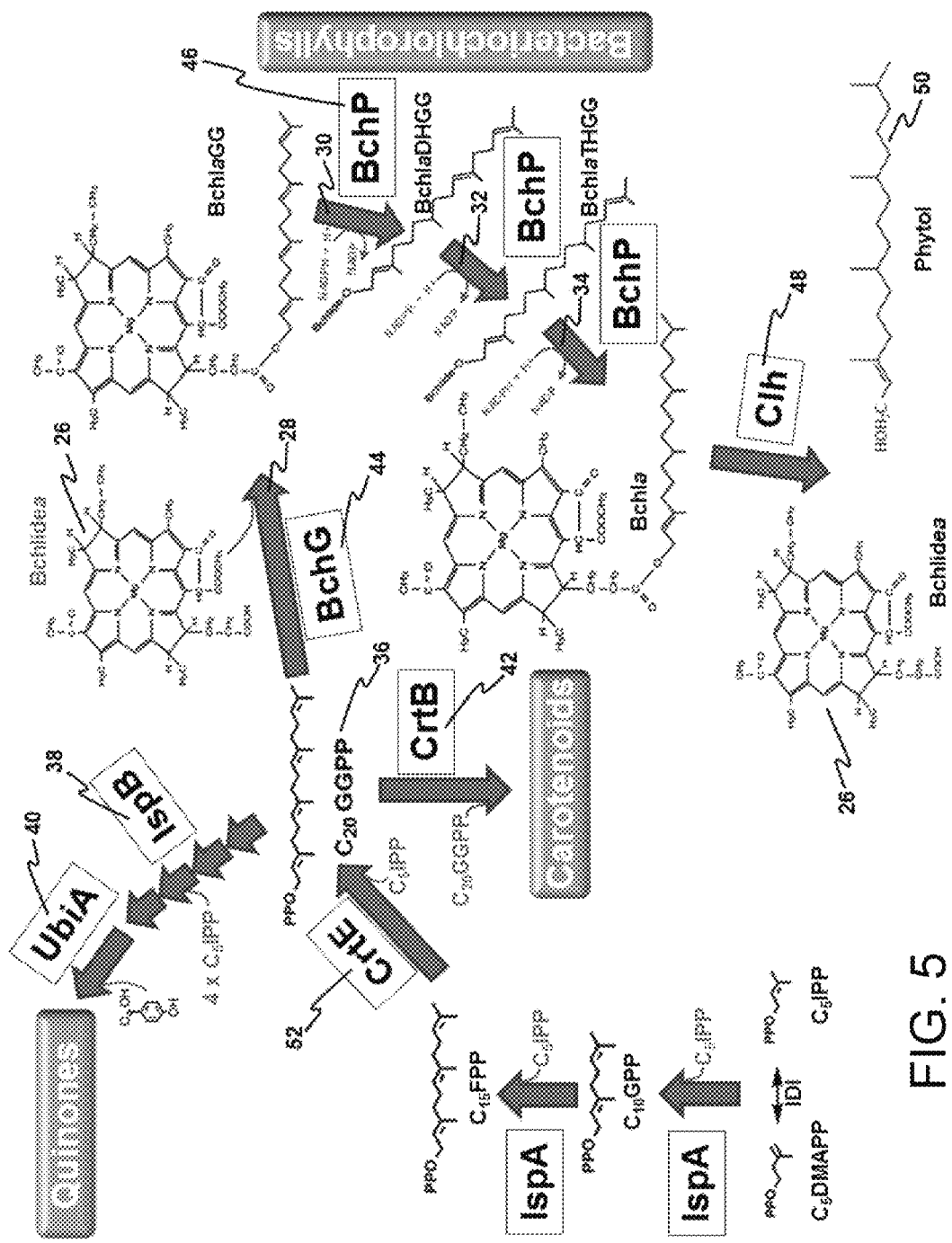
FIG. 5 is a metabolic pathway that utilizes branched, C5 building blocks to synthesize anchors for a variety of co-factors utilized by photosynthetic bacteria and summarizes the biological engineering employed in the phytol-producing strain of *Rhodobacter* that is described as an example in this invention.

An embodiment of the invention is a protocol for designing fuel molecules or precursors of different carbon chain lengths, wherein the molecules are comprised of subunits having the same number of carbons. FIG. 5 illustrates a process for synthesizing the hydrocarbon tail of bacteriochlorophyll by way of repeated additions of five-carbon units, known as isopentenyl pyrophosphate (IPP). The enzymes which catalyze the synthesis of the C20 GGPP from C5 IPP are IspA and CrtE 52.

One initial target set includes the cofactor anchoring moieties which share a common precursor known as geranylgeranyl pyrophosphate (GGPP), that relationship depicted in the central portion of FIG. 5. For example, GGPP is a precursor in the synthesis of phytyl tails which in turn provides an anchoring domain for bacteriochlorophyll, isoprenyl tails of quinones, and carotenoid molecules. The inventors have determined that the interruption in the synthesis pathway of any of these biomolecules results in the overproduction of one or more of the others that result from this common synthetic branch point.

Phytol, having the chemical formula $C_{20}H_{40}O$, is an acyclic, reduced diterpenic alcohol, and is a colorless, high-boiling oil. By attachment through esterification, it becomes part of a mature chlorophyll molecule. As such, Phytol is produced in large quantities by photosynthetic bacteria and algae. Its chemical structure is reproduced below:

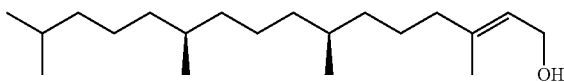 [SMILES: C/C(=C\CO)CCC[C@@H](C)CCC[C@@H](C)CCCC(C)C]

Phytol is the alcohol form anchoring domain of bacteriochlorophyll 20 (FIG. 4) which is produced in extremely large quantities within cells of photosynthetic bacteria. The phytyl tail 22 is the hydrophobic moiety which embeds into the bacterial membrane and serves to position the bacteriochlorophyll at precise locations within the photosynthetic machinery of the cell. Specifically, the Phytyl tail anchors the molecule properly inside membrane proteins (photosynthetic reaction center) involved in light capture and energy conversion.

Several metabolic pathways within the fully sequenced genome of Rhodobacter, can be altered (impaired, augmented, or regulated differently) to increase levels of Phytol within cells or to increase excretion of phytol into the media for its efficient recovery.

FIG. 5 depicts how the enzyme BchG catalyzes the attachment 28 of geranylgeranyl-pyrophosphate (GGPP) to a magnesium-containing protoporphyrin 26 ring in one of the final steps in the synthesis of bacteriochrorophyll in photosynthetic bacteria. The GGPP-derived tail is reduced to its phytyl form by three repeat actions 30, 32, 34 of the enzyme BchP. Engineered variants lacking BchG would not be able to synthesize mature bacteriochlorophyll molecules, and are expected to accumulate free GGPP.

In one embodiment of the invention, BchP is overexpressed in variants lacking BchG in order to ensure full reduction of free GGPP to pyrophosphate form of phytol (reduced C20-PP) that can be used as superior fuel precursor to GGPP itself.

Similarly, FIG. 5 depicts initial steps 42 in the synthesis of carotenoids in Rhodobacter. Disruption of the catalytic activity of CrtB would lead to reduced utilization of GGPP within the cells for carotenoid synthesis and therefore a concomitant accumulation of GGPP of this molecule for harvesting or extracting. Furthermore, the accumulated GGPP is available for increased synthesis of other cofactors like chlorophyll and quinones.

Likewise, genes for enzymes 38, 40, involved in quinone-tail synthesis (IspB and UbiA; FIG. 5) could also be deleted to disrupt the supply of GGPP for this purpose and to favor the use of this intermediate for bacteriochlorphyll biosynthesis.

Figure 4:
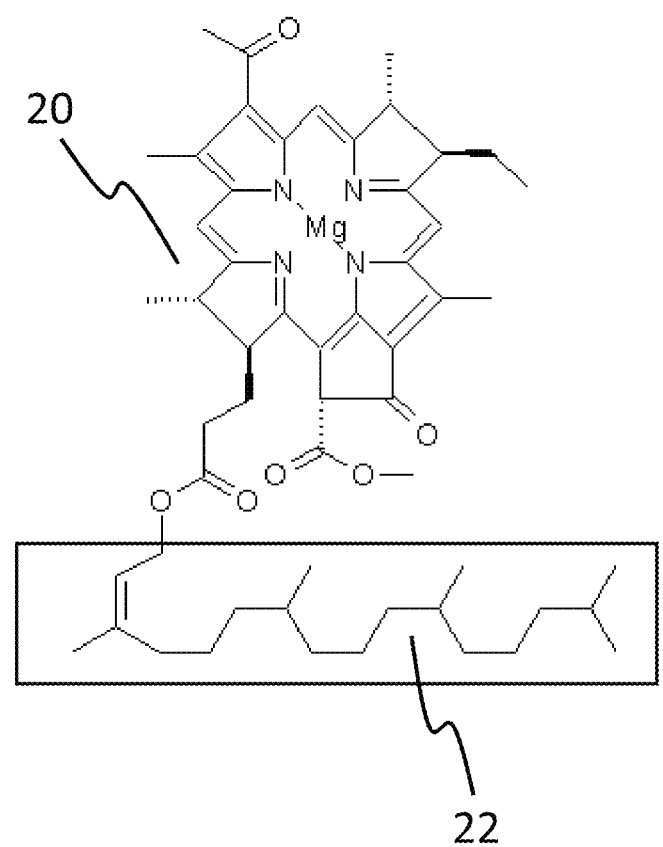
FIG. 4 is a diagram of a mature co-factor (bacteriochlorophyll), including its phytyl tail which serves as an anchor (shown in a box)

Specifically, as depicted in FIG. 5, the inventors have determined that an initial strategy in engineering a Rhodobacter strain capable of overproducing C20 molecules involves two knock-out mutations, thereby producing a double mutant strain. Here, crtB, 42, and bchG, 44, genes are 'knocked-out' to produce a strain that cannot synthesize carotenoids and cannot attach an anchoring tail to protoporphyrin rings. This strain may or may not be photosynthetic. It is sensitive to light damage without carotenoids to regulate photoactivation. Further improvements involve overproduction of the gene bchP, 46, to upregulate the reaction that reduces free GGPP to its phytyl form as depicted in FIGS. 4 and 5.

Photosynthetic variants from this strategy may be produced by complementing this double mutant strain with a plasmid that encodes bchG such that its expression is tightly controlled. This approach allows sufficient photosynthetic variant production for photosynthetic growth, yet still maintains large enough quantities of free GGPP or phytyl tails to accumulate in these cells.

The possibility exists that the overproduction of the fuel or fuel-precursor molecules within the cell could be detrimental to the growth and cultivation of the organism. Isolation or sequestration of the products in vesicles, as discussed supra, will reduce the impact, at the same time provide a means for concentrating the target molecules for later extraction.

In one embodiment of the invention described herein, bacteria are engineered to overexpress BchP to produce larger quantities of the fully reduced phytol moiety. As such, when BchP is expressed in trans and overproduced, observed phytol levels increase (vide infra).

An alternate route for the biosynthesis of phytol is to allow the cofactor to mature fully and then use enzymes to hydrolyze the ester linkage between biofactors and their anchoring moiety. In an embodiment of the invention, chlorophyllase (Clh 48; an esterase), cleaves the hydrophobic membrane-anchoring phytyl chain of chlorophyll from the porphyrin ring, resulting in chlorophyllide 26 and phytol production 50. This embodiment provides a means for producing the reduced alcohol form of the phytyl tail. The activity of these enzymes is well known and has been studied extensively in vitro studies utilizing its natural substrate chlorophyll. Previous investigations only focused on a subset of its activity, the movement of highly colored entities between organic and aqueous layers. This employment of Clh in our production strategies focuses alternatively on the phytol tail resulting from such enzymatic cleavage.

Figure 6:
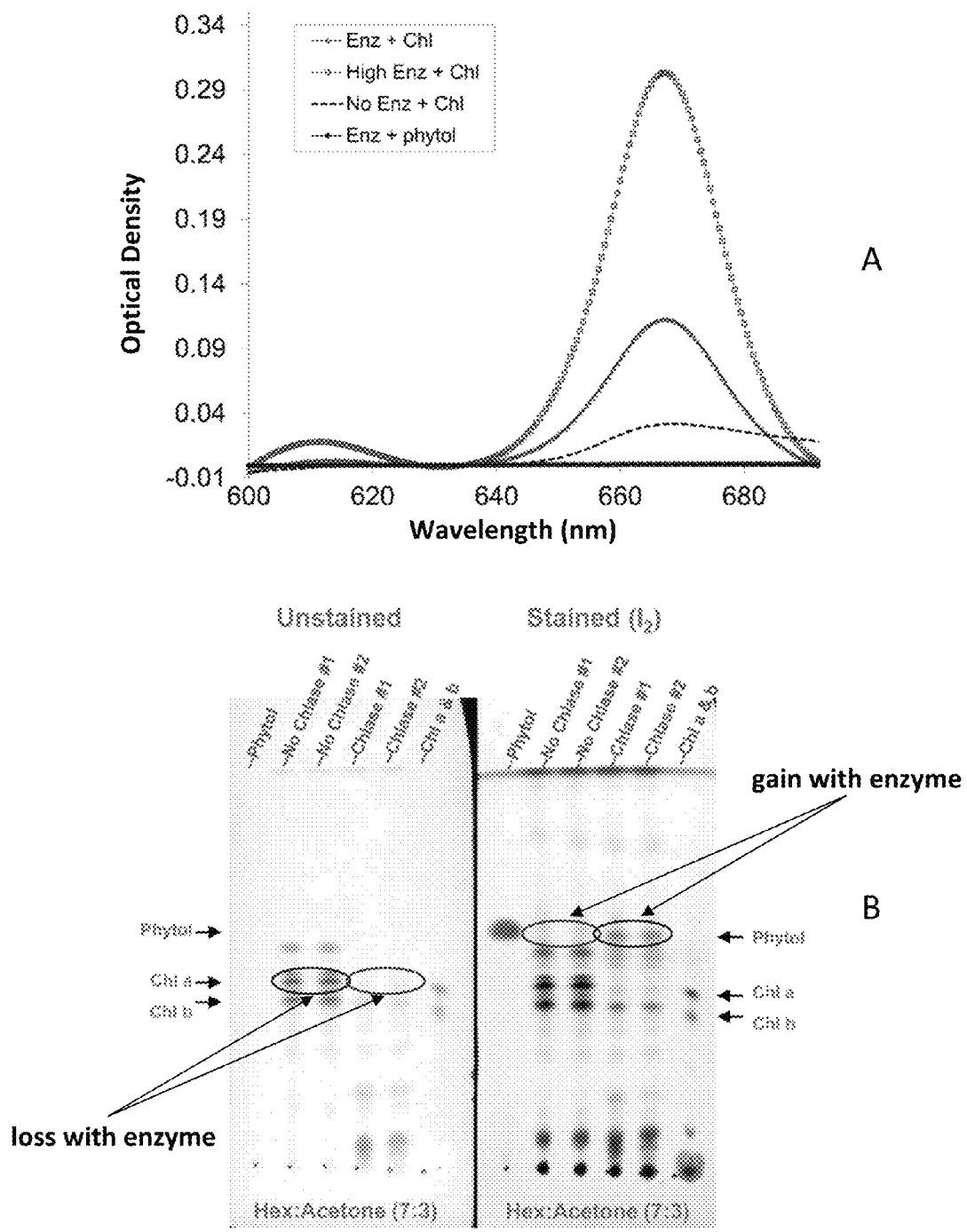
FIG. 6 is a graph and two stained chromatographic plates showing the results of the in vitro enzymatic cleavage of phytol from chlorophyll by chlorophyllase, with the gain of chlorophyllide in aqueous layers (spectra in A) and loss of chlorphyll in organic layers (unstained plate; B, left) and gain of phytol in organic layers (stained plate; B, right)

The inventors have determined that enzymes, such as chlorophyllases perform similar cleavage if given bacteriochlorophyll or chlorophyll as a substrate, producing bacteriochlorophyllide, or chlorophyllide, and phytol, as depicted in FIG. 6. Specifically, FIG. 6A shows that by increasing the amount of chlorophyllase enzyme, substrate cleavage increased in the aqueous layer, resulting in the cleaved Phytol being detected in the organic layer, as depicted in FIG. 6B. As such, the invented method incorporates genes encoding chlorophyllases from different species (such as higher plants) into the cells of photosynthetic prokaryotes to produce engineered bacteria with new capabilities (neofunctionalization) to release phytol moiety from chlorophyll molecules in vivo. In this strategy chlorophyllase gene is maintained on a plasmid DNA that replicates autonomously and thereby in high copy number. Alternatively, a chlorophyllase gene can be inserted into (knocked-in) the genome of photosynthetic prokaryotes (i.e., in the chromosomal DNA and not just the cytoplasm of the cell). This alternative strategy confers stability of the introduced gene but with concomitant low-copy numbers being generated. A second advantage would be that other genes (e.g., bchP) could be expressed from a replicating plasmid at the same time as clh genes.

The highest level of phytol are found within cells of the neofunctionalized strains that are expressing one of the higher plant chlorophyllases, such as that from corn, soybean, *Ginkgo biloba*, *Arabidopsis*, and *Brassica*. When cloned and purified from *Rhodobacter*, the foregoing genes are functionally active and most importantly, these enzymes are active in vivo. Therefore, a mutant strain of the prokaryote containing the chlorophyllase gene is a suitable means for generating phytol. A summary of the engineering employed for the production of phytol in photosynthetic bacteria, utilizing chlorophyllases derived from higher plants, is shown schematically in FIG. 5.

Shorter Carbon-Chain Molecule Targets

Analysis of the pathways presented in FIG. 5 depict ways in which shorter, branched hydrocarbons can be produced in this species with approaches analogous for that of C20 molecules. For instance, accumulation of C15 fuel targets occur with knock-out of the gene for CrtE 52 (and, preferably, the gene for IspB would be knocked-out as well). Similarly, strains accumulating the C10 molecules (like C10-PP) could be engineered by the combination of knock-outs for the genes for CrtE and IspB with down-regulation or knock-out of IspA. An embodiment of the engineered bacteria is IspA knock out along with the incorporation of exogenous IspA in an inducible vector, so as to facilitate a mixture of C10 and C15 moieties. Alternative strategies for production of the C10 intermediate are combining simpler knockout strains with neofunctionalization strategies. C10 molecules are highly sought after biofuel targets as they are likely extremely useful replacements for gasoline. The alcohol form of the C10-PP precursor, C10-OH (known as geraniol or 6,7-dihydrogeraniol) is one such desired biofuel target. Strains accumulating even smaller branched fuel targets (like C5-PP leading to C5-OH or isoprenol) would rely heavily on the tolerance of the organism for the deletion of the gene for IspA.

Strains were designed to overexpress pyrophosphate forms of the C5- and C15-precursors (that could later be converted to the alcohol forms, isopentanol and farnesol) by deleting crtB, bchG, and crtE in *Rhodobacter* in addition to the knock-out of ispA in the same strain for production of the C5 variant. Location of these genes and protocol for knocking out the genes are disclosed infra. These modifications enable the method to precisely design the fuel molecule with regards to three critical factors: carbon chain length, carbon branching, and the oxidation state (oxygen content and unsaturated carbon bonds).

Bacteria that naturally produce cofactor anchors with shorter or less branched chains, such as *Heliobacter* and *Chlorobium*, could be engineered in an analogous approach to produce directly (circumventing pyrophosphate intermediate steps) molecules like farnesol, hexadecanol, phytadienol, and octadecanol, which serve as additional fuel targets. For example, *Heliobacter* synthesizes bacteriochlorophyll c for use in its photosynthetic machinery, and this bacteriochlorophyll naturally has a C15 tail that when cleaved by a chlorophyllase results in farnesol as a product.

Bacterial Strain Engineering Detail

The inventors have determined that cellular levels of phytol are presently the highest in an engineered strain of *Rhodobacter* where a gene in the carotenoid biosynthesis pathway has been deleted and the gene for a chlorophyllase enzyme from soybean (*Glycine max*) is expressed in trans. The design and construction of this engineered strain will be described in detail. Descriptions of the design and construction of other knock-outs and multiply-mutated strains are similar but not included here within. Details for the cloning and utility of chlorophyllases from other plant species (corn, *Arabidopsis*, and *Brassica* species) are also presented since they are active in *Rhodobacter* and phytol accumulates to levels similar to the strain expressing the soybean variant when utilizing them.

Figure 7:
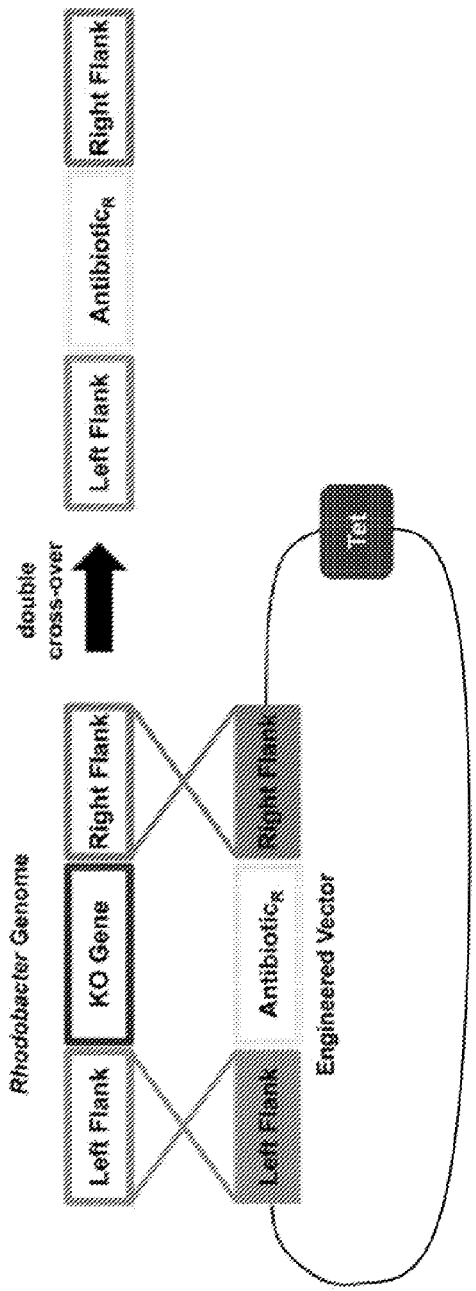
FIG. 7 is a schematic depiction of a strategy to generate knockout mutants.

The crtB-deleted (ΔcrtB) mutant of *Rhodobacter* was constructed using the method of gene knockout (FIG. 7). The basic strategy replaces the chromosomal crtB gene sequence with a selectable antibiotic resistance gene (in this case one conferring resistance to Kanamycin; Km) using the suicide vector pSUP202.

Bacterial Strains

The bacterial strains used in engineering efforts in this study are given in Table 1. *Escherichia* (*E.*) *coli* cultures were grown in rich Luria-Bertani (LB) medium. *Rhodobacter* (*R.*) *sphaeroides* cultures were grown in rich $^G$YCC medium (Taguchi et al., Biochemistry. 1992; 31:10345-55). When appropriate, the media were supplemented with kanamycin (60 μg/ml for *E. coli*; 6 μg/ml *R. sphaeroides*) or tetracycline (15 μg/ml for *E. coli*; 1 μg/ml for *R. sphaeroides*). Gentamycin and spectinomycin are also suitable markers.

Table 1 below lists the specific bacterial strains used.

TABLE 1

| Strain | Description | Source |
|---|---|---|
| *E. coli* | | |
| DH5α | cloning host; F$^-$ endA1 glnV44 thi-1 recA1 relA1 gyrA96 deoR nupG ϕ80dlacZΔM15 Δ(lacZYA-argF)U169, hsdR17($r_K^-$ $m_K^+$), λ- | Purchased from GIBCO-BRL, now Invitrogen, in Carlsbad, California, catalog number 18265-017. |
| S17-1 | host used for conjugal matings; recA pro hsdR RP4-2-Tc::Mu-Km::Tn7 | Constructed from procedures outlined in Simon et al., Nature Biotechnology, Vol. 1, p. 784-791, 1983, incorporated in its entirety by reference. |

TABLE 1-continued

| Strain | Description | Source |
|---|---|---|
| | *R. sphaeroides* | |
| 2.4.1 | wild-type | ATCC 17023 |
| R26 | Actually now called R26.1; naturally isolated carotenoidless strain; point mutation in pucB deems LH2 unstable in this strain | Constructed from procedures outlined in Feher et al., 1978* and Theiler et al., 1985**; the latter incorporated in its entirety by reference. |
| ΔΔ11 | pucBA (Km$^R$) pufQBALMX (Sp$^R$), derivative of wild-type 2.4.1 | ATCC PTA-5921 |
| ΔcrtB | crtB (Km$^R$), derivative of wild-type 2.4.1 | Generated from ATCC 17023 using the protocol disclosed herein. |

*Feher G, Okamura Y. In: Clayton R, Sistrom W, editors. The Photosynthetic Bacteria. New York: Plenum Press; 1978. p. 349-386 (Chapter 19).
**Theiler R, Suter F, Pennoyer J D, Zuber H, Niederman R. Complete amino acid sequence of the B875 light-harvesting protein of *Rhodopseudomonas sphaeroides* strain 2.4.1: Comparison with R26.1 carotenoidless-mutant strain. FEBS Letters. 1985; 184(2): 231-6.

Construction of Suicide Plasmids

To construct this plasmid, PCR products of sequences that flank the crtB gene on both sides in the *Rhodobacter* genome (*R. sphaeroides* strain 2.4.1 genomic DNA used; ATCC 17023) and a gene encoding Kanamycin resistance (from pUC4K; GE Healthcare, Piscataway, N.J. Genbank Accession Number X06404) were joined in an overlapping extension PCR reaction. The primers used to amplify the flanking regions and Km to enable the joining reaction are listed in Table 2. The joined product was cloned nondirectionally into pSUP202 (Ap$^R$Cm$^R$Tc$^R$) (Simon et al., Bio/Technology. 1983; 1:37-45)—a mobilizable plasmid that cannot be replicated in *R. sphaeroides*—using EcoRI sites designed into the outer-most primer set, at the ends of the flanking regions, to create pSUP202crtBKO (Ap$^R$Tc$^R$Km$^R$).

TABLE 2

| Gene Amplified | Primer Names | Primer Sequences (5'→3') | Amplicon size (bp) | Notes |
|---|---|---|---|---|
| Phytoene dehydrogenase (PD) | PD.top | GAATTCAAAATGCCCTCGAT CTCGCCCGC (SEQ. 1) | 1566 | EcoRI at 5' end |
| | PD.bot | TCATTCCGCGGCAAGCCTT TCAGC (SEQ. 2) | | Overlaps 5' end of Km |
| Km$^R$ | Kan.top | GGCTTGCCGCGGAATGAGG GGGGGGAAAGCCACGTTG (SEQ. 3) | 1286 | Overlaps 3' end of PD |
| | Kan.bot | GCCCAGTCCATGTTCAT CCCCCGGATCCGTCGACC (SEQ. 4) | | Overlaps 5' end of TSP |
| Tryptophan-rich sensory protein O (TSP) | TSP.top | ATGAACATGGACTGGGCTC TTTTCCTC (SEQ. 5) | 486 | Overlaps 3' end of Km |
| | TSP.bot | GAATTCAAATCAGGCGCGG GCTTCGGG (SEQ. 6) | | EcoRI at 3' end |

Construction of Deletion Strain ΔcrtB

Following transfer of pSUP202crtBKO to the *R. sphaeroides* recipient strain ATCC 17023 via conjugation with *E. coli* donor strain S17-1 (Simon et al., ibid), Km$^R$Tc$^S$ exconjugants that had lost the crtB gene as a result of a double-crossover event were selected. In brief, matings were performed with small nitrocellulose filter discs placed atop 2XTY agar plates at 37° C. for 3 hours using an equal ratio of donor cells to recipient cells. The mating mixture was removed from the filter in 1 mL of MR26 medium (Table 3) and washed twice in the same.

TABLE 3

Recipe for *R. sphaeroides* medium MR26
Use 20 mL of A, B, and C per L of MR26 medium;
add 1 mL D per L after autoclaving.

| | | |
|---|---|---|
| A. Potassium phosphate buffer: | 1 M, pH 6.8, adjusted with KOH or H$_3$PO$_4$ | |
| | K$_2$HPO$_4$ | 115 g/L |
| | KH$_2$PO$_4$ | 44.9 g/L |
| B. Ammonium succinate: | 1 M, pH 6.8 | |
| | Dissolve 118 g succinic acid in 500 mL H$_2$O. Adjust pH to 6.8 with ammonium hydroxide. Add H$_2$O to 1 L. | |
| C. Concentrated base (per L): | Add the following in order: | |
| | Na$_2$EDTA$2H$_2$O | 11.16 g |
| | (NH$_4$)$_6$Mo$_7$O$_{24}$$4H$_2$O | 0.0093 g |
| | FeSO$_4$$7H$_2$O | 0.099 g |
| | "Metals 44" | 50 mL |
| | MgSO$_4$ | 14.5 g |
| | CaCl$_2$ | 2.5 g |
| Metals 44 (per L): | FeSO$_4$$7H$_2$O | 5.0 g |
| | Na$_2$EDTA$2H$_2$O | 6.5 g |
| | ZnSO$_4$$7H$_2$O | 10.9 g |
| | MnCl$_2$$4H$_2$O | 1.3 g |
| | CuSO$_4$$5H$_2$O | 0.392 g |
| | CoCl$_2$$6H$_2$O | 0.200 g |
| | H$_3$BO$_3$ | 0.114 g |
| D. Vitamins: | (per L to prepare 1000x stock solution): | |
| | Nicotinic acid | 3.0 g |
| | Nicotinamide | 3.0 g |
| | Thiamine HCl | 6.0 g |
| | Biotin | 0.12 g |
| | Filter sterilize and store at 4° C. | |

The entire conjugal reaction was plated on MR26/Tc agar plates. Selection for desired deletion mutants proceeded on rich $^G$YCC agar plates. Routine molecular biology procedures were used as per Sambrook et al., (Molecular cloning: A laboratory manual. 1989. New York. Cold Spring Harbor Press). Replacement of the crtB gene with the Km$^R$ cassette was confirmed by PCR with primers, listed in Table 4 (in 5'→3' format), that produce amplicons that bridge the regions between the flanking sequences and the antibiotic resistance cassette.

TABLE 4

Oligos used in PCR reactions to confirm
allelic exchange of crtB and Km(5'→3').

| | |
|---|---|
| TSP_cnfrm.top | GCAGGGGGCAAGGGGGGC (SEQ. 7) |
| Kan_cnfrm.bot | GCCATCCTATGGAACTGCCTCG (SEQ. 8) |

TABLE 4-continued

Oligos used in PCR reactions to confirm allelic exchange of crtB and Km (5'→3').

| | |
|---|---|
| Kan_cnfrm.top | CTCTGGCGCATCGGGCTTCC (SEQ. 9) |
| PD_cnfrm.bot | CCTCCTGCAGATGGGGTGGG (SEQ. 10) |

Construction of Chlorophyllase Expression Plasmids

Using expression strategies optimized for membrane protein production in *Rhodobacter* (e.g., Laible et al., 2011; subject of U.S. Pat. No. 6,465,216 B2), the genes for several higher plant chlorophyllases were isolated from mRNA or cDNA libraries. In the case of soybean chlorophyllase-3, the gene was derived from cDNA made from mRNA that was extracted from 7-day-old seedlings grown in the inventors' laboratory. Here, 3-4 dime-sized sections of non-cotyledonous leaves from cold-stressed soybean plants were homogenized after flash freezing in liquid nitrogen. Total RNA was isolated using a kit (RNeasy; Qiagen; Valencia, Calif.). A library of cDNA was prepared using priming oligonucleotides comprised of random decamers with reagents from a reverse transcriptase kit (RETROScript; Ambion, now Invitrogen; Austin, Tex.). The chlorophyllase gene (981 bp) was amplified from the resulting cDNA pool using the Accuprime Pfx DNA polymerase (Invitrogen; Carlsbad, Calif.) and a reaction mix that was supplemented with dimethylsulfoxide to about 2 percent. Oligonucleotides used to produce clonable fragments with and without the native stop codon are listed in Table 5. The most successful reaction conditions used a 'touchdown' amplification strategy where the annealing temperature of the PCR reaction was stepwise-lowered from about 58° C. to about 52° C. over the course of the initial 20 cycles.

Genes for chlorophyllases from other plants were cloned similarly, with main differences in the strategies coming from the origins of the DNA used in the amplification reactions. The chlorophyllase-3 gene from corn was amplified from a commercial cDNA library obtained from BioChain (Catalog C1634330; Hayward, Calif.). The *Arabidopsis thaliana* chlorophyllase-1 gene was amplified from a cDNA library that was a gift of Dr. Kate Warpeha, a Research Assistant Professor at the University of Illinois at Chicago. And, due to the limited availability of source material, the *Brassica oleracea* chlorophyllase-1 was synthesized for us by Blue Heron Biotechnology (Bothell, Wash.). In the last case, the sequence was modified from the AT-rich version found in the plant to favor codons used preferentially by *Rhodobacter* in expressing genes from its GC-rich genome. The sequence of the modified *Brassica oleracea* gene is attached in its entirety as Table 6.

TABLE 5

| Source | Primer Name | Primer Sequence (5'→3') |
|---|---|---|
| Glycine max (soybean) | Gm3.top | CTGTACTAGTGGAGGATAGTAATGCAAAACTTTGCAGAATC TCATCAACTTTCAG (SEQ. 11) |
| | Gm3_nostop.bot | TGTAAGATCTTCACAGAAAAGAGTCAAATTTGATCTCCACT GG (SEQ. 12) |
| | Gm3_stop.bot | TGTAAGATCTCAGAAAAGAGTCAAATTTGATCTCCACTGG (SEQ. 13) |
| Zea mays (corn) | Zm2.top | CTGTACTAGTGGAGGATAGTAATGAACCTCGCGTCCGCGG TGCG (SEQ. 14) |
| | Zm2_nostop.bot | TGTAAGATCTAGCTATCGCTTTCTCATCTCCAAACTCCACC ACGG (SEQ. 15) |
| | Zm2_stop.bot | TGTAAGATCTCTAAGCTATCGCTTTCTCATCTCCAAACTCC ACCACGG (SEQ. 16) |
| Arabidopsis thaliana | At1.top | CTGTACTAGTGGAGGATAGTAATGGCGGCGATAGAGGACA GTCCAACGTTTTCCTC (SEQ. 17) |
| | At1_nostop.bot | TGTAAGATCTGACGAAGATACCAGAAGCTTCTTCCAACTCA GG (SEQ. 18) |
| | At1_stop.bot | TGTAAGATCTCTAGACGAAGATACCAGAAGCTTCTTCCAAC TCAGG (SEQ. 19) |
| Brassica oleracea | Bo1.top | CTGTACTAGTGGAGGATAGTAATGGCGGGGAAGGAGGAC AGTGAGACG (SEQ. 20) |
| | Bo1_nostop.bot | TGTAAGATCTGACGAGATAACCAGAAGCCTCTTCCAGCTC CGG (SEQ. 21) |

The genes were cloned into plasmid pRKPLHT1 Dpuf (as described in U.S. Pat. No. 6,465,216 B2, and incorporated herein by reference) for expression with a C-terminal, 7-member histidine tag using the restriction enzymes SpeI and BglII purchased from Promega (Madison, Wis.) in accordance with routine molecular biology protocols described in Sambrook et al. (ibid). The integrity of each of these constructs was confirmed by DNA cycle sequencing. Following transfer of the resulting expression plasmid, pRKGmcIhHT1Dpuf, to the *R. sphaeroides* recipient strains (e.g., ΔcrtB described above or other hosts listed in Table 2) via conjugation with *E. coli* donor strain S17-1, $Tc^R$ transconjugants were selected on minimal MR26/Tc medium. Here, conjugal matings proceeded as described for that of the suicide vectors, except for the ratio of recipient to donor was adjusted to 50 and only 0.5 percent of a typical reaction was plated directly to rich $^G$YCC medium. These differences reflect the relative ease by which the broad-host-range expression plasmid can be transferred and maintained stably in trans.

TABLE 6

Complete sequence (5'→3') of the modified *Brassica oleracea* gene
(modifications from the wild-type sequence are shown in capital letters).

(SEQ. 22)

ACTAGTGGAGGATAGTAatggcggggaaggaggacagtgagacgttttctcggcggcaactcctttggcgtttgag ttaggcagccttccaacaaccgtgatccccgcagacccgtcggcaaccgatttgaccgcacctCCGaagcctgtaat aatcacctccCCGaccgtcgccggaacttaccccgtcgtcCTGttcttccatggattctatcttcgtaactacttct actctgatgttattaaccacgtagcttctcatggctacattgttGTGgccCCGcagctttgcaagattttgccgccg ggagggcaagtggaagtggacgatgctggaaaagtgATCaactggacttcgaaaaacctcaaagctcacctcCCGag ttcaGTGaacgctaatggcaactacaccgcactcgtgggtcatagccgcggtggtaaaaccgcgtttgcggttgcgC TGggccacgccgcaacaCTGgacccatccatcaagtttTCGgctcttgtaggaatagatCCGgttgcaggaatcagc aaatgcataCGCaccgatcccgaaatcCTGacgtacaaaccggaatcattcgacctggacatgccggttgcagtgat cggtacgggtctcggaccgaagagtaacatgctgatgCCGCCGtgcgcaCCGgcggaagtgaaccatgaggagtttt atattgagTGCaaggctacgaagggacatttcgtggctgcggattacggacatatggatatgttggacgataatttg cccggttttgtcgggtttatggcgggtTGCatgTGCaagaacggtaaacgcaaaaagagtgagatgagaagctttgt tggtggaattgtggttgcgtttctaaagtatagtatatggggtgaaatgtcagagattcgacagatttgaaggatc cttctgtttctccagcgaggcttgatccttcgccggagctggaagaggcttctggttatctcgtctagAGATCT.

Figure 8:
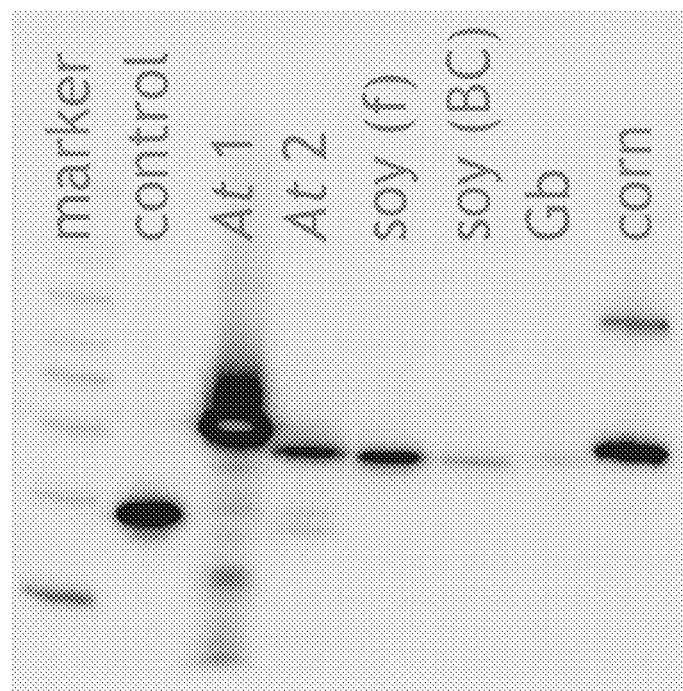
FIG. 8 is an immunoblot (probed with anti-poly-his) showing expression of chlorophyllase in *Rhodobacter* membranes.

Expression of the various chlorophyllase genes in *Rhodobacter* was examined using small-scale (usually between 25 milliliter to one liter) semi-aerobic cultures; in this embodiment, about 80 milliliters were used. Cellular fractionation studies revealed that the chlorophyllase enzymes were localized to the membrane fraction. Expression levels were quantified using SDS-PAGE and immunoblot techniques (utilizing an anti-polyhistidine antibody) that have been described in the literature, including Laible et al., Foreign Gene Expression in Photosynthetic Bacteria, The Purple Phototrophic Bacteria, Springer-Verlag, New York, 2008; Laible et al., Membrane protein production in *Rhodobacter*, a practical guide, Weinheim: Wiley-VCH, 2011. Levels of expression in *Rhodobacter* membranes of several higher plant chlorophyllases are shown in FIG. 8. FIG. 8 is an immunoblot (anti-poly-his) showing expression of higher plant chlorophyllase genes in the membrane fraction of *R. spheroides*. At=*Arabidopsis thaliana*; soy=soybean; Gb=*Ginkgo biloba*; corn=corn; (f)=field; and (BC)=Bio-Chain. *Brassica oleracea* data is not shown but expresses to levels similar to that for corn.

Growth and Harvest Detail of Engineered Strains

Wild-type and mutant strains of *R. sphaeroides* were grown under chemoheterotrophic conditions (semi-aerobic, dark, 33° C., 2 L of media in 2.8 L Fernbach flasks, 125 rpm) on $^G$YCC medium. Strains carrying expression plasmids (clh, bchP, or other genes) were supplemented with tetracycline (1 μg/ml). Culture turbidity was monitored with a Klett-Summerson (Klett) colorimeter. Wild-type cultures reached stationary phase after 2-3 days of incubation with Klett values approaching 300. Harvesting (by centrifugation at 10,500×g for 7 minutes) typically occurred at this point. To remove retained media components, the cell pellets were washed once in Buffer 1 (10 mM Tris, 100 mM NaCl, pH 7.8) in the original centrifuge bottles and cells were repelleted. Washed cell pellets were resuspended in a smaller volume of Buffer 1, transferred to a 50 mL conical tubes, and pelleted at 10,000×g. Samples were lyophilized (Freezone 4.5; Labconco, Kansas City, Mo.) over a period of 2-3 days. Dried samples were weighed and stored at −80° C. freezer.

Purification of Chlorophyllases for In Vitro Functional Studies

Figure 9:
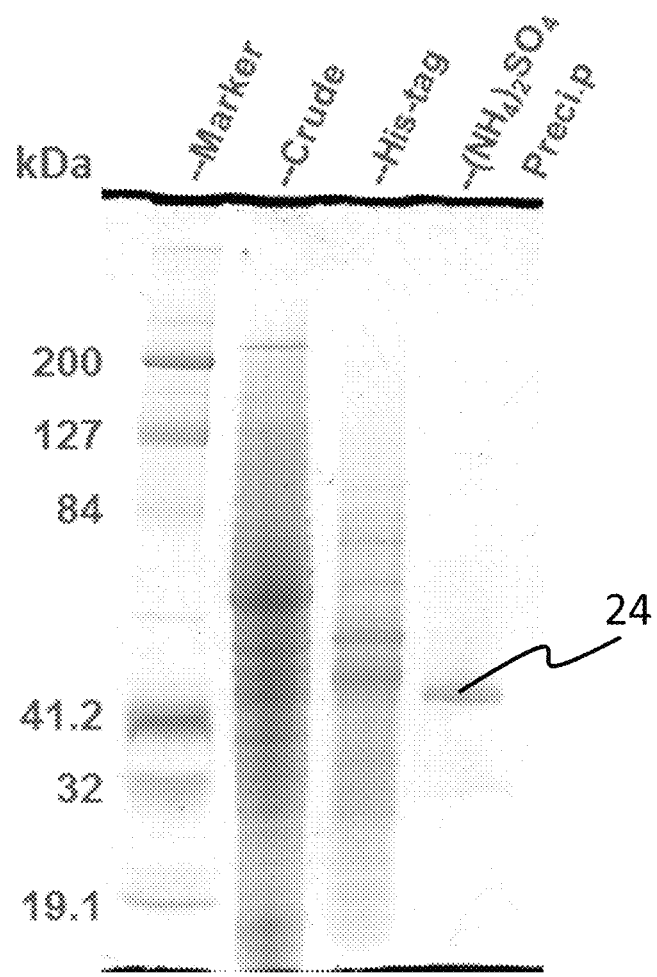
FIG. 9 is a Coomassie-blue stained protein gel (SDS-PAGE) showing the purity of various samples of chlorophyllase used for in vitro characterization.

Generic and rapid methods for solubilization and purification of chlorophyllase enzymes from *Rhodobacter* membranes were employed for the isolation of protein used in reactions outside of the cell to confirm the activity of chlorophyllase enzymes produced in bacteria as described in Laible et al. Journal of Structural and Functional genomics, 2004, 5: 167-172. Utilizing the polyhistidine tag engineered into the expression vector, chlorophyllase enzymes solubilized using a detergent lauryldimethylamine-oxide (LDAO) were purified in an initial step using immobilized metal affinity chromatography. Further purification of the chlorophyllase samples was achieved efficiently through ammonium sulfate precipitation. Although some variation existed in the level of ammonium sulfate that could be tolerated by the different chlorophyllase variants, most remained in solution at concentrations up to 40 percent and readily precipitated at concentrations above 55 percent. The foregoing two-day procedure yields 10 to 20 milligrams, usually between 13 to 15 milligrams quantities of most chlorophyllases with purities in the range of 85 percent to 99 percent, usually between 93 percent to 96 percent. (FIG. 9).

In Vitro Chlorophyllase Reaction Detail

In the foregoing embodiment, chlorophyllases were purified from intracytoplasmic membrane fractions and tested in reactions performed in phosphate buffer, pH 7.0, at 37° C. while agitating. Substrates consisted of chlorophylls or bacteriochlorophylls that had been extracted from spinach with acetone or from *Rhodobacter* cells with methanol, respectively. Reactions were performed successfully using crude pigment extracts or purified (bacterio)chlorophyll species that had been separated from the crude pigment pools using protocols based upon ion-exchange chromatography protocols known in the literature and as described in Oelz J., Methods in Microbiology, Volume 18, Gerhard Gottschalk, Academic Press Inc., London, 1985, 257-282. Substrates dissolved in acetone were introduced into the activity assays, and chlorophyllases were shown to tolerate up to 75 percent organic solvent in the reactions and were the most active in 20 percent acetone. Additions of a 6:4 (v/v)

hexane:acetone mixture simultaneously quenched the reactions and separated starting material and products. Unreacted substrate and cleaved phytol tails partitioned into the organic phase, comprised mainly of hexane. Cleaved (bacterio)chlorophyllides were found exclusively in the aqueous phase. Reaction progress was monitored after quenching by the loss of the strong absorption of (bacterio)chlorophyll in the organic phase, the gain of (bacterio)chlorophyllide absorption in the aqueous phase, and/or the appearance of phytol bands in thin-layer chromatography separation of samples from the organic fraction (vide infra; the best mobile phase employed a 7:3 hexane to acetone mixture). Enzymes proved stable and could be stored for long periods at 4° C.

Organic Extraction Detail of Isoprenols

Extracts for isoprenol analysis were prepared from 0.5 g of freeze dried cells using a 15 mL Dounce Tissue Grinder (Kontes; Vineland, N.J.). The samples were homogenized using 10 mL of acetone and other chemicals purchased from Sigma Aldrich and Fisher Scientific. The extract solution was separated from the cell debris by centrifugation at 10,000×g for 10 mins. The supernatant was removed, and the extraction of the cell debris pellet was repeated four additional times. The supernatants were combined and concentrated to a final volume of 4 mL by rotary evaporation (Model 421-1651, Labconco, Kansas City, Mo.). Analogous methodology was used when analyzing subcellular fractions for the presence of isoprenols.

Extraction of isoprenols from spent medium used a slightly altered solvent system since acetone is soluble in water. A myriad of solvent extraction systems are known, including those described in Arkus et al., Mechanistic analysis of wheat chlorophyllase. Archives of Biochemistry and Biophysics. 2005; 438:146-55, incorporated herein by reference. Approximately 2 L of medium was extracted with a total of 350 mL of 6:4 (v/v) hexane:acetone to produce an immiscible layer which was removed. The same volume of medium was reextracted with 8:2 (v/v) hexane:acetone. The organic layer from this second extraction was combined with the first and concentrated in a rotary evaporator to a final volume of 3 mL. Any final solvent adjustments were done with 8:2 (v/v) hexane:acetone.

Spectral Analysis Detail

In one embodiment, composition from highly pigmented extracts from the *R. sphaeroides* strains were analyzed spectroscopically for comparison of pigment composition. This organic concentrate contains all of the bacteriochlorophylls, carotenoids, and pigment-biosynthesis intermediates that were contained within the cell at the time of the harvest. These concentrates should exclude bacteriochlorophyllides that would have partitioned into aqueous layers. Concentrates were diluted so as to be within the dynamic range of the UV-vis-near IR spectrophotometer (for example, a 1:20 dilution). Absorption spectra were recorded in quartz cuvettes at room-temperature by a UV-1601 PC instrument (Shimadzu; Kyoto, Japan).

Quantitative Phytol Analysis Detail

In one embodiment, for each strain, 2 µL samples were spotted onto silica gel 60 thin-layer chromatography (TLC) plates (EMD; Gibbstown, N.J.) and were resolved with a solvent system containing hexane:ethyl acetate (normally in a ratio of 7:2). Control samples were included on every plate. Typically, 2 µL of 0.05 percent chemically-synthesized phytol (SAFC; Catalog 30979LJ; St. Louis, Mo.) served as a quantitative marker and improved the consistency of staining. After separation was completed, the solvent was evaporated, and the dried plates were developed in an iodine chamber. TLC plates were scanned using a PowerLook 1100 scanner (UMAX; Dallas, Tex.) and the bands were then quantified by using the imaging software ImageJ (NIH).

Anchoring Domain Isolation Detail

Figure 10:
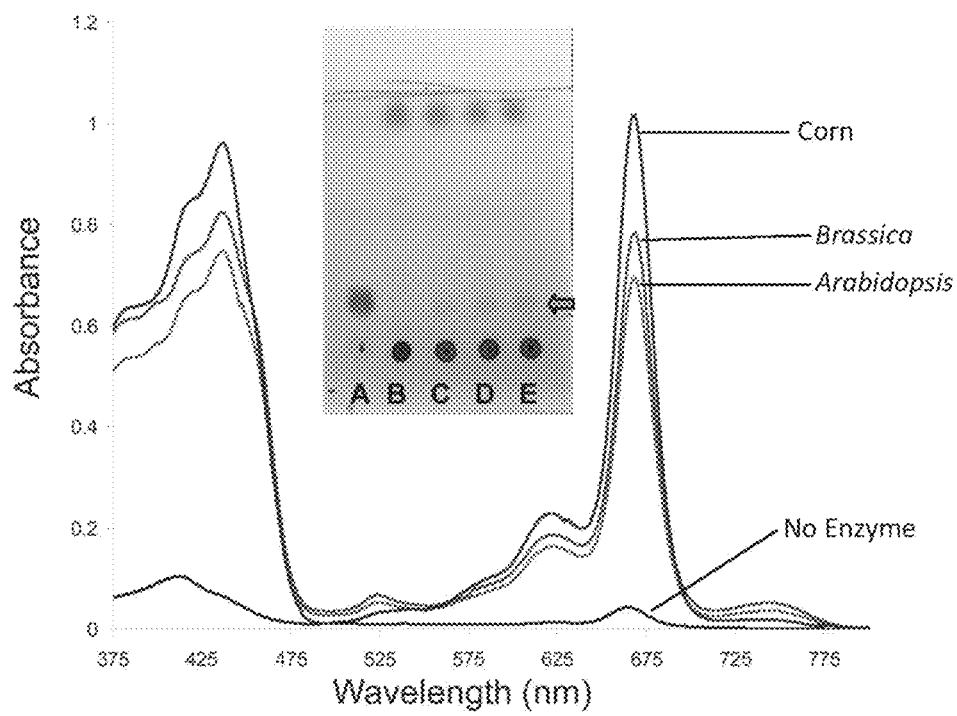
FIG. 10 is a graph (main) and stained chromatographic plate (inset) showing in vitro phytol production by three different purified plant chlorophyllases.

Phytol has never been shown previously to accumulate in *Rhodobacter* species. Past in vitro studies on chlorophyllases described in the literature focused on the movement of highly colored entities (chlorophylls and chlorophyllides) from organic to aqueous phase and did not attempt to track the movement of the phytol tail as it was produced as a result of enzymatic cleavage. Thus, methods for extraction and the means to track phytol moiety during in vitro enzyme reactions were developed. So, in vitro reactions were performed with chlorophyllases produced by *Rhodobacter* strains. Of the three enzymes that could be readily purified (those from corn, *Arabidopsis*, and *Brassica*), all proved active in the conversion of (bacterio)chlorophyll into (bacterio)chlororophyllide and phytol. FIG. 10 is a Comparison of the in vitro activities of *R. spheroides*-produced higher plant chlorophyllases. Absorption intensity of chlorophyllide species produced by the enzymatic cleavage (main). TLC resolution of phytol ( ) observed in the organic layer after a 10 minute reaction (inset). Relative phytol band intensities are reported in parentheses. Under standard conditions with 10 minutes incubation, the corn variant seems slightly more active than either the *Brassica* or *Arabidopsis* variants (FIG. 10). The soybean variant was not included in these in vitro studies since its expression was shown to be lower on immunoblots (FIG. 8), and focus was placed on the three most highly expressed chlorophyllases. Purification of the chlorhphyllase from *Glycine max* would be, most likely, challenging.

Figure 11:
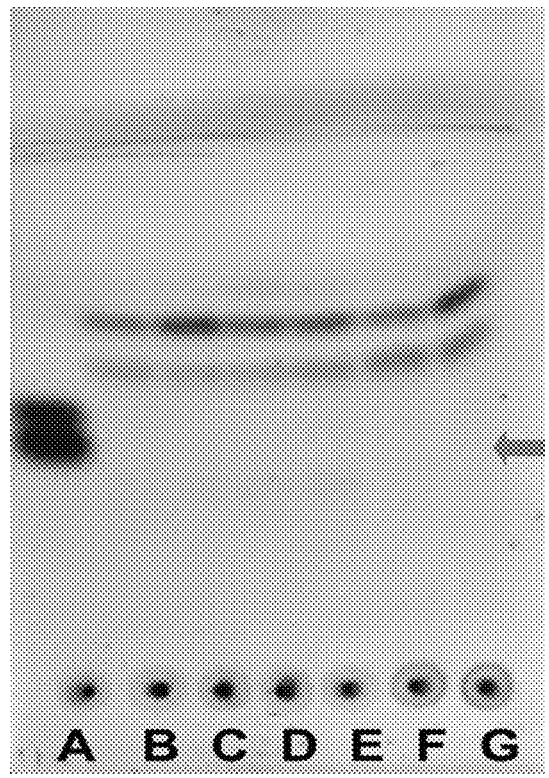
FIG. 11 is a stained chromatographic plate showing the absence of phytol in organic extracts from knock-out mutants and control strains.

Robust extraction methodologies emerged from work with in vitro reactions and tests with phytol-doped *Rhodobacter* cells. All engineered strains constructed were checked for levels of phytol produced. As one of the initial checks of methodology used for extraction and characterization of engineered strains, none of the control strains and none of the knock-outs by themselves produced any phytol (FIG. 11). Thus, the inventors found that gene interruptions alone are not enough to drive phytol accumulations in engineered strains (likely strain accumulating GGPP).

Along with the control strains, more than 30 engineered strains of *Rhodobacter* were grown in 2 L semi-aerobic culture, harvested, and lyophilized (Table 7). These strains resulted from knock-out, overproducing, and neofunctionalized approaches. The majority of the strains examined were ones that are the results of combinations of engineering approaches. Organic extraction of the dried material showed a myriad of pigment compositions consistent with studies designed to alter cofactor biosynthesis pathways. Phytol was found in the cells of many of these strains. Strains were screened blindly and grouped into four phytol production categories for comparison purposes (Table 7). FIG. 11 depicts an analysis of organic extracts from knock-out mutants and control strains. Phytol (⇐) is not observed. FIG. 12 depicts an analysis of neofunctionalized strains of *Rhodobacter* producing levels of phytol (⇐) that are categorized as 'high'. The best strains in this category converted 1-2% of cell mass into phytol. TLC plate was developed with 7:2 hexane:ethyl acetate. The highest levels of phytol are found within cells of the neofunctionalized strains that are expressing one of the higher plant chlorophyllases (FIG. 12). When neofunctionalized with chlorophyllase, the ΔcrtB produces higher levels of phytol than the equivalent wild-type (2.4.1) or R26 variants. The higher levels in ΔcrtB are likely a result of shuttling more C20 precursors (like geranylgeranyl pyrophosphate) towards bacteriochlorophyll production since carotenoid synthesis has been interrupted by the knockout. The higher level in ΔcrtB in comparison to R26 (a naturally occurring carotenoidless mutant) is likely due to the differences in the protein complement of these strains. In addition to being a blue-green carotenoidless mutant, R26 is also known for its inability to produce functional forms of one of the antennae complexes of the photosynthetic apparatus. Bacteriochlorophyll production, and hence phytol production, appears to be linked to the presence of the proteins that sequester it. Without the proteins that normally bind this cofactor, the production may be down-regulated. This hypothesis is corroborated by the data for neofunctionalized strains of the ΔΔ11 host (missing even more of the complexes that normally bind bacteriochlorophyll).

TABLE 7

| Phytol Levels | Strain Name | Mutant Type | | |
|---|---|---|---|---|
| | | KO | OP | Neo |
| Null | 2.4.1 | | | |
| | R26 | | | |
| | ΔΔ11 | | | |
| | ΔbchGΔispA | XX | | |
| | ΔbchG | X | | |
| | ΔbchGΔcrtBΔispA | XXX | | |
| | ΔbchGΔcrtB | XX | | |
| | ΔcrtB | X | | |
| | R26[pRKGbClhHT1Dpuf] | | | X |
| | ΔcrtB[pRKGbClhHt1Dpuf] | | | X |
| | ΔcrtBΔbchG[pRKbchPHT1Dpuf] | XX | X | |
| Low | ΔbchG[pRKbchP] | X | X | |
| | ΔΔ11[pRKZmClhHT1Dpuf] | | | X |
| | ΔΔ11[pRKBioChGmClh3HT1Dpuf] | | | X |
| | ΔΔ11[pRKZmClh2HT1Dpuf] | | | X |
| | 2.4.1[pRKbchP] | | X | |
| | ΔΔ11[pRKBoClhHT1Dpuf] | | | X |
| | ΔΔ11[pRKfGm3ClhHT1Dpuf] | | | X |
| | ΔcrtB[pRKbchP] | X | X | |
| | ΔΔ11[pRKbchP] | | | X |
| Medium | ΔΔ11[pRKZmClh2HT1Dpuf] | | | X |
| | ΔΔ11[pRKZmClh21D41Dpuf] | | | X |
| | ΔcrtB[pRKBoClhHT1Dpuf] | X | | X |
| | R26[pRKBoClhHT1Dpuf] | | | X |
| | R26[pRKJenClh3HT1Dpuf] | | | X |
| | R26[pRKAtClh2HT1Dpuf] | | | X |
| high | 2.4.1[pRKBioChGmClh3HT1Dpuf] | | | X |
| | R26[pRKBioChGmClh3HT1Dpuf] | | | X |
| | 2.4.1[pRKfGmClh3HT1Dpuf] | | | X |
| | R26[pRKZmClh2HT1Dpuf] | | | X |
| | ΔcrtB[pRKAtClh2HT1Dpuf] | X | | X |
| | R26[pRKAtClh1HT1Dpuf] | | | X |
| | ΔcrtB[pRKZmClh2HT1Dpuf] | | | X |
| | 2.4.1[pRKBoClh1HT1Dpuf] | | | X |
| | ΔcrtB[pRKAtClh1HT1Dpuf] | X | | X |
| | 2.4.1[pRKZmClh2HT1Dpuf] | | | X |
| | ΔcrtB[pRKBioChGmClh3HT1Dpuf] | X | | X |
| | ΔcrtB[pRKfGmClh3HT1Dpuf] | X | | X |

Table 7, abbreviations: KO = Knock-out; OP = overproducing; Neo = neofunctionalized; Gb = Ginkgo biloba; Bo = Brassica oleracea; Zm = Zea mays; At = Arabidopsis thaliana; f = field; BioCh = BioChain; Clh = chlorophyll hydrolase (chlorophyllase)

Chlorophyllase activity in vivo is not affected by fusions of an affinity peptide to the C-terminus. Results from strains expressing identical chlorophyllases with different small tags/fusions at the C-terminus useful in quantification or purification experiments yield the same results. The inventors observed that polyhistidine- and 1D4-tagged versions exhibit the same phytol levels within cells as the non-tagged equivalents.

Figure 13:
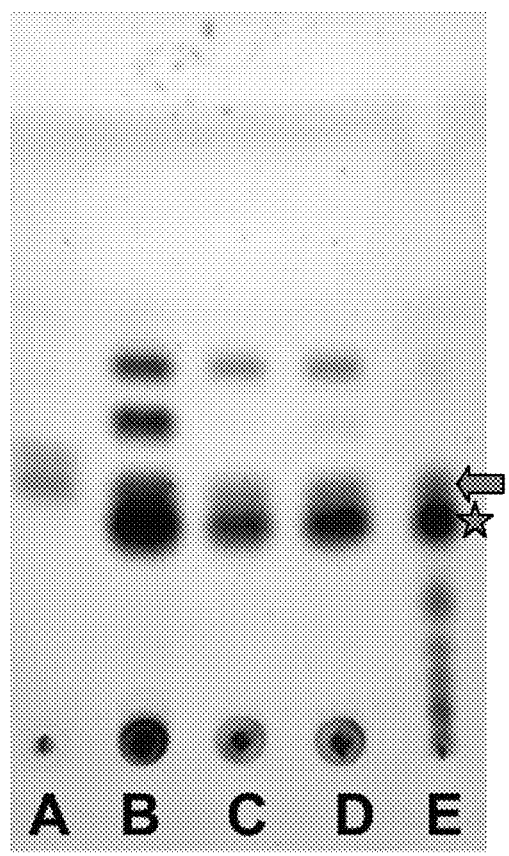
FIG. 13 is a stained chromatographic plate showing localization of phytol produced by a neofunctionalized strain.

Since the isoprenyl tail of bacteriochlorophyll serves to anchor it within cellular membranes and, more specifically, within hydrophobic proteins that are membrane localized and because of its strong hydrophobic nature, expectations were high that most of the phytol produced in engineered strains of Rhodobacter would be localized to membrane fractions. FIG. 13 shows the localization of phytol in neofunctionalized strains once it is hydrolyzed from bacteriochlorophyll in vivo. This figure depicts the analysis of the localization of phytol ( ⇐ ) produced by the neofunctionalized strain 2.4.1[pRKB73 ZmClh21D41Dpuf]. Phytol was found in many places. In addition to strong signals from Rhodobacter membranes, the molecule can be found associated with cellular debris components (e.g., large fragments of cell wall and outer membranes that comprise a good fraction of the cell debris pellet, in addition to cells that remain unbroken after passage multiple times through a microfluidizer device specifically designed to rupture these cells). Of note and of some surprise was the presence of phytol in the spent medium from this culture (FIG. 13, lane E). When quantifying yields of phytol in various fractions, nearly 50 percent of it is found in the medium. In our exemplary strain of ΔcrtB[pRKfGmClh3HT1Dpuf] the yield of phytol within the cell was 0.46 percent of the dry weight of the cells and the yield of phytol exported into the medium was 0.44 percent of the dry weight of the cells. The total yield of extracted phytol was 0.9 percent of the dry weight of the cells. With estimated extraction efficiencies between 50 percent and 80 percent, the predicted absolute yield of phytol produced within this engineered strain ranges between about 0.5 and 50 percent of the dry weight of the cells, preferably about 5 and 10 percent and typically about 1 to 2 percent of the dry weight of the cells.

Figure 14:
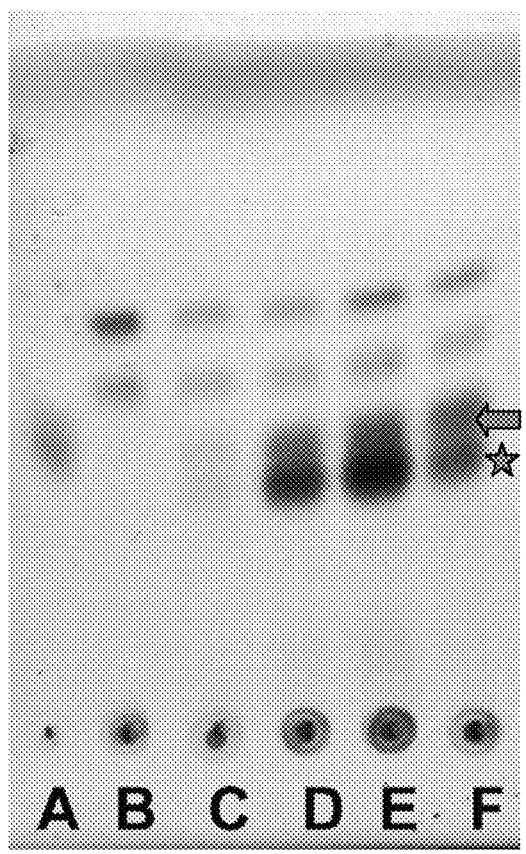
FIG. 14 is a stained chromatographic plate comparing production levels of phytol in strains expressing different chlorophyllase genes.

The in vivo activity of the various chlorophyllases does not scale linearly with their observed expression yields. Thus, the in vivo activities and abilities of various plant chlorophyllases to hydrolyze bacteriochlorophyll vary to a large extent. This result comes from the comparison of the levels of phytol produced in the knock-out mutant ΔcrtB when it is expressing different higher plant chlorophyllases (FIG. 14). The relative integrated intensity of the phytol band is shown in parenthesis. Here, the strain expressing the soybean chlorophyllase produced approximately the same amount of cellular phytol as the strain expressing corn chlorophyllase. This is in sharp contrast to the observed relative levels of expression of the enzymes (FIG. 8) where soybean chlorophyllases were barely detectable in Rhodobacter membranes while corn chlorophyllase was expressed at much higher level.

Figure 15:
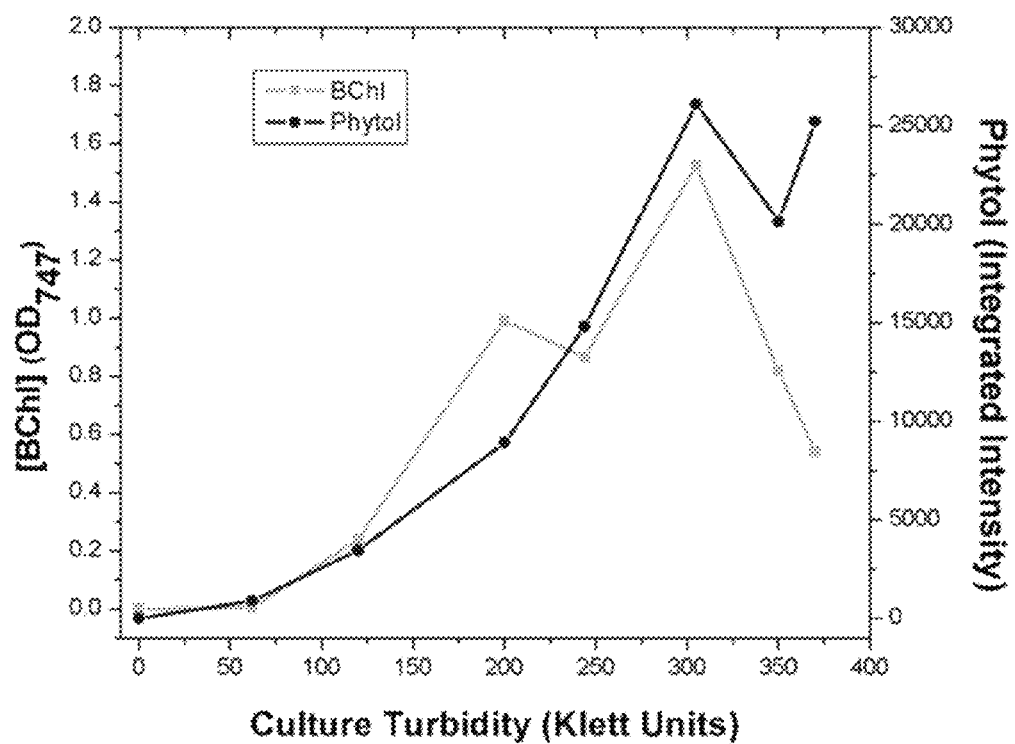
FIG. 15 is a graph depicting relative phytol and bacteriochlorophyll levels in an engineered strain of *Rhodobacter* as a function of growth as measured by culture turbidity.

Phytol appears stable once produced within cells, and its production scales with culture turbidity (FIG. 15). In neofunctionalized strains, the accumulation of phytol appears to track with bacteriochlorophyll synthesis, except when cells reach the late log phase of growth wherein bacteriochorophyll level rapidly declines while the level of phytol remains fairly high with some degree of fluctuation.

The inventors perceive the potential protection afforded by protein which binds bacteriochlorophyll. If chlorophyllases are active within cells and all of the substrate was available for catalysis/hydrolysis, then bacteriochlorophyll would not accumulate to high levels once chlorophyllase genes were expressed. This is not the case. Protocols are envisioned to increase phytol production by releasing or converting these inaccessible substrate pools for chlorophyllase action during or just prior to cell lysis and/or extraction. When stored in a dark bottle (glass) at room temperature, (capped) the produced phytol is stable for at least two years. As such, phytol is stable once produced within cells.

Other bands on TLC plates of organic extracts from engineered Rhodobacter strains show that other C20 molecules are accumulating. Of particular interest is the lower band (gray star/asterisks) that appears in extracts from neofunctionalized strains expressing higher plant chlorophyllases. Its presence is reproducible, and the relative intensities of it and the band attributed to phytol are variable (FIG. 12). The inventors have identified this band as a non-reduced form of phytol known as geranylgeraniol (GG-OH; C20 branched alcohol with four double bonds). Data that support this conclusion are shown in FIG. 16A where phytol and GG-OH standards are compared to extracts from a chlorophyllase-expressing strain. The results strongly suggest that the upper band corresponds to phytol (as it co-migrates with one of the isomers of standard phytol) and the lower band corresponds to geranylgeraniol (as it co-migrates with the standard geranylgraniol). Thus the method enables the production of oxidized forms of phytol in strains that express chlorophyllases. Although mature bacteriochlorophyll a molecules have phytyl tails with only one double bond, the C20 moiety initially attached from geranylgeranyl pyrophosphate (GGPP) has four double bonds and is subsequently turned into a mature bacteriochlorophyll by multiple rounds of reduction by BchP (FIG. 5). It is possible that immature forms of bacteriochlorophyll serve as substrate for chlorophyllases and are cleaved in vivo producing pools of relatively-more-oxidized, long-chain, branched alcohols (e.g., GG-OH).

Some strains yield to higher levels of GG-OH than phytol (including the strain whose data are reported in FIG. 12). Although iodine stains hydrocarbon molecules randomly, it has higher affinity for unsaturated hydrocarbons and aromatics than saturated or less unsaturated hydrocarbons. Thus, for the same amount of GG-OH and phytol spotted onto a TLC plate, the GG-OH band would be expected to be much more intense. Estimates for GG-OH in the example strain of ΔcrtB[pRKfGmCIh3HT1Dpuf] suggest that its levels are approximately equal to that of phytol. Combining production levels of the two C20 alcohols (both the reduced phytol and the oxidized GG-OH), the yields of target molecules that could serve as potential diesel surrogates approaches between 2.5 and 4 percent of the dry weight of the cells.

Figure 16:
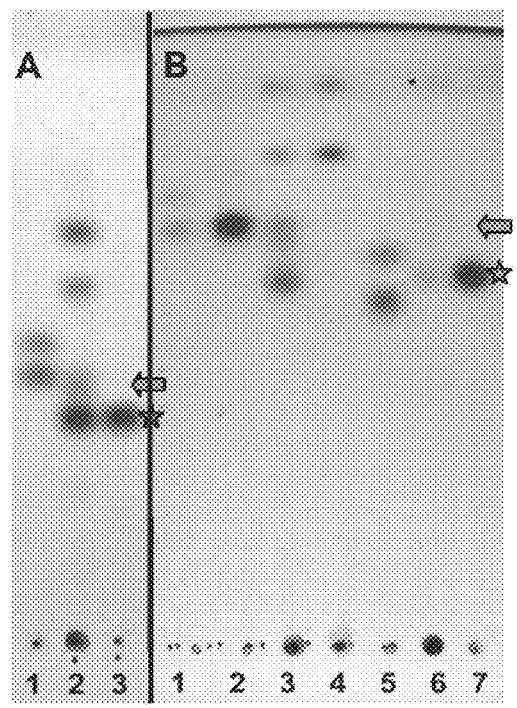
FIG. 16 is a stained chromatographic plate showing the presence of phytol and geranylgeraniol in organic extracts from engineered strains.
Figure 17:
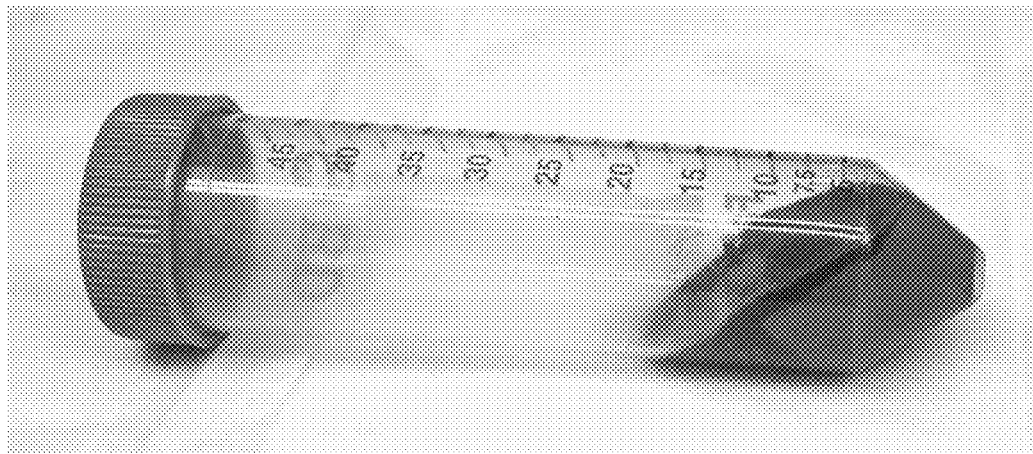
FIG. 17 is a picture of the cell and residual pellet from a culture of an engineered strain of *Rhodobacter* producing phytol showing a black layer covering the cell pellet.

FIG. 16 is a Comparison of the banding pattern of phytol (⇐) and geranylgeraniol (☆) control samples to signals observed with organic extracts from engineered strains of *Rhodobacter*. Identical mobile phases were used in each of the TLC analyses shown but the plate shown in panel B was longer and run for a longer time for better band separation. FIG. 16B seeks to determine the identity of a black residue that has been observed to be exported in large quantity from engineered strains generated in this research effort. The residue forms a black layer on top of the cell pellet after centrifugation (FIG. 17). This residue has been collected, lyophilized, extracted and analyzed by TLC. The dominant species is again that which runs at an $R_f$ value that is the same as that of GG-OH. Additional experiments are underway to understand this phenomenon and to quantify levels that are exported using this mechanism. GG-OH is not a molecule that would be an initial target for biofuels production. However, an alternative approach is reducing GG-OH to phytol in cells. The inventors have engineered strains that overproduce BchP. BchP is an enzyme that reduces geranylgeranyl tails of immature bacteriochlorophyll to phytyl tails of mature bacteriochlorophyll in *Rhodobacter* (FIG. 5). Combinations of neofunctionalized and overproducing strains should result in an engineered form of *Rhodobacter* where the dominant C20 alcohol that accumulates is that of phytol. This approach will minimize the amount of GG-OH found in organic extracts from engineered strains.

Qualitative Phytol Analysis of the Mutant Strains

Figure 18:
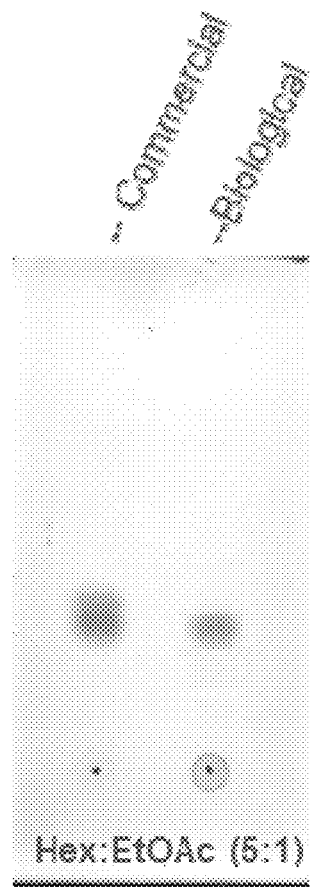
FIG. 18 is a chromatographic plate comparing isomeric purity between commercial phytol and phytol produced biologically.
Figure 19:
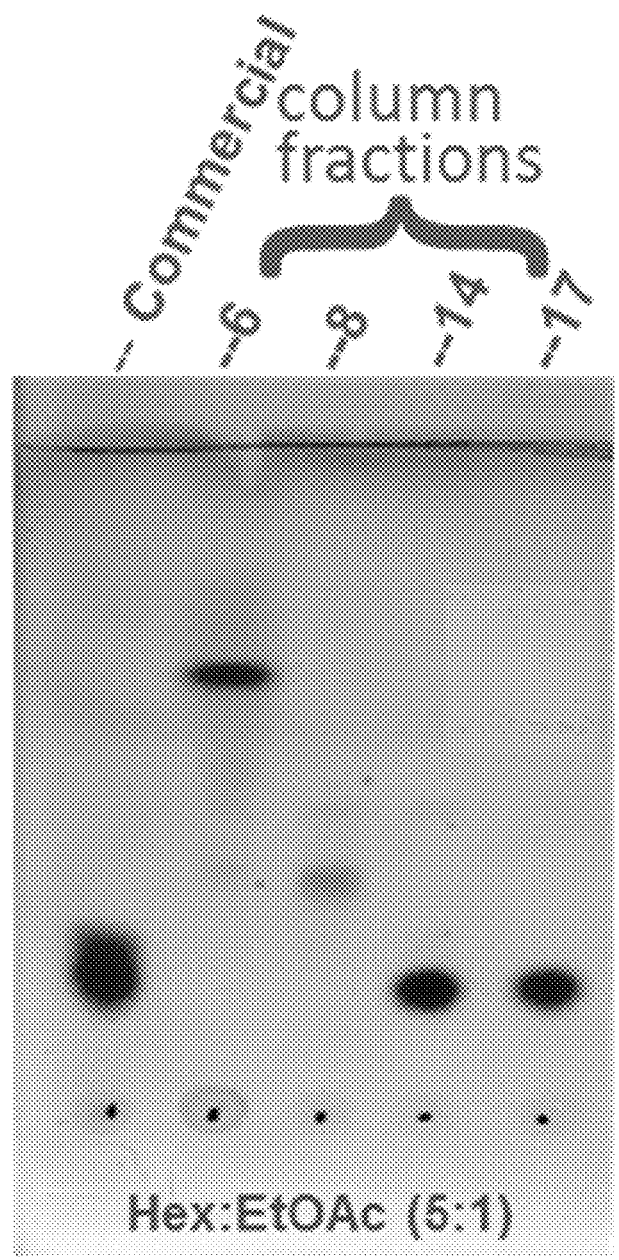
FIG. 19 is a chromatographic plate comparing isomeric purity between commercial farnesol and farnesol produced biologically.

In one embodiment, each strain, in two-microliter-sized samples and controls, was spotted onto silica gel 60 thin-layer chromatography (TLC) plates purchased from EMD in Gibbstown, N.J. The plates were subsequently resolved with a solvent system containing hexane:ethyl acetate, normally in a ratio of 7:2. Staining consistency is typically improved with the addition of two microliters of 0.05 percent chemically-synthesized phytol purchased from SAFC located in St. Louis, Mo.; also serving as quantitative markers. After separation, the solvent was evaporated, and the dried plates were developed in an iodine chamber. The TLC plates were scanned using a PowerLook 1100 scanner purchased from UMAX in Dallas, Tex., and the bands were then quantified using the imaging software ImageJ from the NIH. FIGS. 18 and 19 show that the biosynthesized phytol and farnesol are more isomerically pure when compared to the commercial products.

Alternative Methods and Combination Methods

Engineered strains that are producing the largest amounts of phytol presently combine methods for gene deletion, gene over-expression, and/or novel gene introduction. To increase further the utility of these strains, additional engineering strategies will be necessary. One such approach will be that of gene 'knock-in', where additional copies of a gene or new genes are placed back into the chromosome of the organism. The knock-in mutation strategies follow the protocol outlined for 'knock-out' mutations described above, except the region where the new gene will reside are noted. The new gene must either carry its own promoter and regulatory elements or have the aforementioned incorporated appropriately into an existing operon. The presence of the desired 'knock-in' mutant can be confirmed by the addition of antibiotic resistance cassette along with the gene introduced or by the loss of antibiotic resistance if the strategy incorporates a gene at the site where one was previously removed and antibiotic resistance introduced.

Geranylgeraniol (GG-OH, which is a C20-branched alcohol with three double bonds), is a non-reduced form of phytol. Oxidized forms of phytol can be produced in strains that express chlorophyllases. The C20 moiety initially attached from geranylgeranyl pyrophosphate (GGPP), containing three double bonds, can be converted to a mature bacteriochlorophyll, having a phytyl tail with only one double bond, by multiple rounds of bchP reduction. Oxidized forms would result if the chlorophyllases cleave the phytol tail prior to the complete reduction of the tail by BchP.

Geranylgeraniol is generally not an initial target for biofuel production. However, an alternative approach to the invented method would be to use prokaryotes to generate Geranylgeraniol, an alcohol, and then reduce it to phytol either by in vitro chemical reduction or by overexpression of BchP in the cells expressing chlorophyllase. The expression of extra amounts of the enzyme BchP in strains expressing clh gene(s) in trans is possible by transferring one of the genes to the chromosome (via a knock-in approach vide supra) or employing strategies for polycistronic expression from a single plasmid or use of two or more compatible replicating plasmids within the host strain.

Inventors' data suggests that pools of other phytol-related, branched C20 alcohols, accumulate in the engineered strains, but are inaccessible, as depicted in FIGS. 16 and 17. If these pools are made accessible, releasing or converting these substrate pools for chlorophyllase action during or just prior to cell lysis and/or extraction will result in an increase in overall phytol production in the invented method.

Alternatively, varying lengths of naturally occurring hydrocarbon chains can also be a viable source for biofuel molecules. These hydrocarbon chains can exist in any organism that has photosynthetic capabilities. Specifically, *Heliobacter* species uses bacteriochlorophyll g, which possesses a C15 hydrocarbon tail, to harvest and convert light energy. If plant chlorophyllases can utilize this form of bacteriochlorophyll, the foregoing species could be used as a source of reduced farnesol.

*Rhodobacter* Features Facilitating Efficient Fuel Extraction

Figure 20:
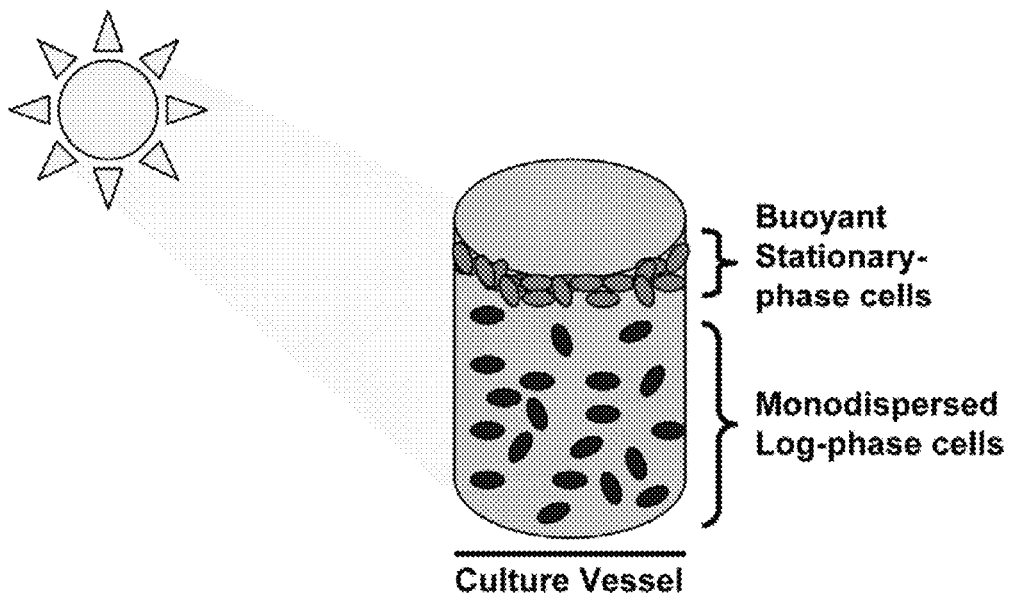
FIG. 20 is a schematic depiction of one embodiment of the system in operation, in accordance with features of the present invention.

In operation of another embodiment of the invented system, and as schematically depicted in FIG. 20, a large culture vessel housing is utilized to increase the mass of engineered purple, non-sulfur bacteria growing photosynthetically, so as to produce (large) quantities of fuel or fuel-precursor molecules. These fuels are stored internally and render the cells buoyant.

Production of sufficient quantities of fuels would allow for passive separation of fresh growing cells from mature cells as the latter would float to the top of the vessel and could be removed easily by skimming off, pumping out or otherwise removing the top layer and replenishing with media. A vessel like this could likely operate in continuous mode for long periods. In addition, using the described pathways, the fuel molecules would be more compatible than ethanol or biodiesel in gasoline, diesel, or jet fuel. In a means of making the extraction of fuels housed internally within *Rhodobacter* cells as efficient as possible, harvested cells are lysed non-mechanically by addition of lytic bacteriophage, such as, RS1, to a final multiplicity of infection of 0.5 to 10, as described in the literature, including Abeliovich et al., Bacteriophages of *Rhodopseudomonas spheroides*: Isolation and Characterization of a *Rhodopseudomonas spheroides* Bacteriophage. Journal of Virology. 1974; 13:1392-1399, which is incorporated by reference in its entirety.

Comparison of Physicochemical Properties of Biofuel Molecules with the Standard Fuels To establish the produced biofuel compounds (C5, C10, C15, and C20 alcohols) as fuels, the compounds were procured from Sigma Chemical Company (St. Louis, Mo.) and subjected to a standard set of fuel property tests and were compared to two established fuels: diesel #2 and biodiesel (soy methyl ester). Table 8 shows carbon, hydrogen, and oxygen content; heat of combustion, cetane number, viscosity, boiling/distillation temperature, vapor pressure, and density. Fuel properties were measured by established ASTM methods at validated testing facilities (indicated in Table 8). The primary goal is to produce fuels in a similar range as diesel #2. Biodiesel is an approved blend component for diesel #2 and is listed as a comparison to establish ranges of accepted fuel properties.

The carbon, hydrogen, and oxygen content establish the chemical formula. Oxygen content that is too high can limit the performance of the fuel. The C-5 alcohol has a higher oxygen content than biodiesel. C-10, C-15, and C-20 alcohols have lower oxygen contents than biodiesel. Mixtures of the claimed biofuel moieties can be produced that have a lower oxygen content than biodiesel. Blends of the claimed biofuel moieties with diesel #2 can be produced that have a lower oxygen content than biodiesel.

The heat of combustion represent how much energy is available from the fuel for performing work. The C-5 alcohol has a slightly lower heat of combustion than biodiesel. C-10 and C-15 alcohols have heats of combustion higher than biodiesel but slightly lower than diesel #2. C-20 alcohol has a higher heat of combustion than diesel #2. Mixtures of the claimed biofuel moieties can be produced that have the similar heat of combustion as diesel #2. Blends of the claimed biofuel moieties with diesel #2 can be produced that have the similar heat of combustion as diesel #2.

The cetane number is a measure of a fuel's ignition delay. Ignition delay is the time period between the start of fuel injection and pressure increase during fuel combustion. Higher cetane fuels have shorter ignition delay periods than lower cetane fuels and will perform better in compression devices such as diesel engines. C-5, C-10, and C-15 alcohols have cetane numbers lower than diesel #2. The C-20 alcohols have a cetane number within the specification range for diesel #2. Mixtures of the claimed biofuel moieties can be produced that have the similar heat of combustion as diesel #2. Blends of the claimed biofuel moieties with diesel #2 can be produced that have the similar heat of combustion as diesel #2.

Viscosity is a measure of the ability of a fluid to flow. The boiling/distillation temperature (50 percent level) is a measure of the vaporization of the fuel into the gas phase. C-5 has a viscosity in the range of diesel #2 and biodiesel. C-10, C-15, and C-20 alcohols have viscosities higher than diesel #2 and biodiesel. Blends of the claimed biofuel moieties with diesel #2 can be produced that have the similar viscosities as diesel #2.

Density is a measure of the amount of fuel molecules in a given volume. A lower density requires a larger fuel tank. In the case of ethanol, the mileage penalty in comparison to gasoline can be attributed to the lower density of ethanol. C-5, C-10, C-15, and C-20 alcohols have densities similar to diesel #2 and biodiesel. Mixtures of the claimed biofuel moieties will have densities similar to diesel #2. Blends of the claimed biofuel moieties with diesel #2 will have densities similar to diesel #2.

Density is a measure of the amount of fuel molecules in a given volume. A lower density requires a larger fuel tank. In the case of ethanol, the mileage penalty in comparison to gasoline can be attributed to the lower density of ethanol. C-5, C-10, C-15, and C-20 alcohols have densities similar to diesel #2 and biodiesel. Mixtures of the claimed biofuel moieties will have densities similar to diesel #2. Blends of the claimed biofuel moieties with diesel #2 will have densities similar to diesel #2.

Combustion occurs in the gas phase so boiling/distillation is an indicator of the fuel to burn efficiently. The C-5 alcohol has a lower boiling/distillation temperature than diesel #2. C-10 and C-15 alcohols have boiling/distillation temperature in a similar range as diesel #2. The C-20 alcohol has a boiling/distillation temperature higher than diesel #2 but still lower than biodiesel. Mixtures of the claimed biofuel moieties can be produced that have similar boiling/distillation temperature as diesel #2. Blends of the claimed biofuel moieties with diesel #2 can be produced that have the similar boiling/distillation temperature as diesel #2.

Vapor pressure (298 K) is a measure of the amount of the fuel present in the gas phase at ambient temperature. It must be balanced between too high, which could damage the engine and too low which can delay combustion initiation. Vapor pressure can vary widely with chemical combustion. C-5, C-10, and C-20 alcohols have vapor pressures that are between biodiesel and diesel #2. The C-15 alcohol has a higher vapor pressure than diesel #2. Mixtures of the claimed biofuel moieties can be produced that have similar vapor pressure as diesel #2. Blends of the claimed biofuel moieties with diesel #2 can be produced that have similar vapor pressure as diesel #2. All biofuel moiety mixtures and blends will have vapor pressure closer to diesel #2 than biodiesel.

Diesel #2 is a blend of several fuel moieties. Blends enable fuels to have physical properties, such as those summarized in Table 8, to exist over a range. Blends enable the fuel to perform over a range of environmental conditions, especially temperature. The biofuel moieties produced by the invented method are designed to be used as mixture of the components in blends with diesel #2 or other established fuels in existing engines and combustion devices. The blend range can be very wide (1-85 percent). As combustion devices and engines are redesigned to adapt to available fuels, mixtures of the claimed biofuel moieties may be utilized as 100 percent renewable, drop-in biofuels.

These results indicate that the biofuel moieties have physical fuel and combustion properties within the range of established fuels. From these results, it was established that the biofuel moieties can be blended with established fuels and retain fuel and combustion properties within working ranges. It should be noted that even biodiesel from any feedstock is currently used as a blending agent rather than a pure fuel. Furthermore, mixtures of the biofuel moieties can be designed to produce a targeted fuel or an intermediate for blending with established fuels.

TABLE 8

| Fuel Property/ Combustion | Justification | Diesel # 2 | Biodiesel (Soy methyl ester) | C-5 Prenol[£] | C-10 Geraniol[¥] | C-15 Farnesol[§] | C-20 Phytol[∈] | Method |
| --- | --- | --- | --- | --- | --- | --- | --- | --- |
| Carbon Content [wt percent] | Composition | 87 | 76.74 | 69.66 | 75.82 | 80.27 | 80.8 | A |
| Hydrogen Content [wt percent] | Composition | 13 | 12.01 | 11.61 | 13.9 | 12.41 | 13.15 | A |
| Oxygen Content [wt percent] | Composition | 0 | 11.25 | 18.73 | 10.28 | 7.12 | 6.05 | A |
| Heat of Combustion [KJ/Kg] | Energy content of fuel available | 42,000 | 37,400 | 36,104 | 41,415 | 41,790 | 43,664 | B |
| Cetane Number | Ignition Delay controlling fuel performance in a compression engine | 40-45 | 46-55 | 12.62 | 28.05 | 21.26 | 42.35 | C |
| Viscosity (Pa – S) at 298 K | Flow into engine, droplet breakup and mixing | 0.00135 | 0.00649 | 0.0022 | 0.0121 | 0.0143 | 0.0522 | D |
| Boiling/Distillation Temp (K)- 50 percent Recovery | Capability to vaporize and burn efficiently | 243 | 362 | 141.1 | 212.8 | 289.4 | 335.6 | E |
| Density (kg/m3) at 298K | Density impacts mass and momentum flow rates into the combustion chamber | 820 | 883 | 858.9 | 825.6 | 883.3 | 850.10 | F |

TABLE 8-continued

| Fuel Property/ Combustion | Justification | Diesel #2 | Biodiesel (Soy methyl ester) | C-5 Prenol[£] | C-10 Geraniol[¥] | C-15 Farnesol[§] | C-20 Phytol[∈] | Method |
|---|---|---|---|---|---|---|---|---|
| Vapor pressure (Pa) at 298K | Balanced to prevent cavitation damage of injector (too high), delay in spray atomization and mixing (too low) | 1000 | 40 | 658.61 | 481.29 | 7599 | 481.29 | G |

*Presented at: Sibendu Som, Douglas E. Longman "Nozzle Fow Characterization of Alternate Fuels for Compression Ignition Engine Applications", presented at SAE 2011 World Congress, Apr. 12$^{th}$, 2011, Detroit MI
A) Measured using Test Method: ASTM E191 by Phoenix Chemical Laboratory, Chicago IL
B) Measured using Test Method: ASTM D240 by Phoenix Chemical Laboratory, Chicago IL
C) Measured using Test Method: ASTM D6890-04 by Southwest Research Institute, San Antonio TX
D) Measured using Test Method: ASTM D445 by Phoenix Chemical Laboratory, Chicago IL
E) Measured using Test Method: ASTM D86 by Phoenix Chemical Laboratory, Chicago IL
C) Measured using Test Method: ASTM D1475 by Southwest Research Institute, San Antonio TX
C) Measured using Test Method: ASTM D2879 by Southwest Research Institute, San Antonio TX
$^£$C-5 test molecule was 3-methyl-2-buten-1-ol (Catalog W364703)
$^¥$C-10 test molecule was 3,7-Dimethyl-1-octanol (Catalog W239100)
$^§$C-15 test molecule was 3,7,11-Trimethyl-2,6,10-dodecatrien-1-ol (Catalog W247804)
$^∈$C-20 test molecule was 3,7,11,15-Tetramethyl-2-hexadecen-1-ol (Catalog W502200)

It is to be understood that the above description is intended to be illustrative, and not restrictive. For example, the above-described embodiments (and/or aspects thereof) may be used in combination with each other. In addition many modifications may be made to adapt a particular situation or material to the teachings of the invention without departing from its scope. Specifically, the inventors envision that the biofuel generated via the invented method and system can be used in neat form, a blend of different carbon length fuel, or as a "drop-in" form, in other words mixed with fuel generated from other sources (e.g. fossil fuel sources or other non-biofuel/nonrenewable fuel sources), to provide a suitable combustible mixture.

In light of the foregoing, embodiments of the system include engineered strains which produce a single chemical species of interest, or more than one chemical species. The inventors envision the development of microscopic refineries where moieties are simultaneously produced and blended within the same cell, or in the case of different cells, within the same broth. Depending on market push, production of a single chemical species may be one desired result, but production of a mixture of species may have as great or larger value to the fuel industry. This is due to the fact that most fuels on the market today are mixtures and are designed that way to improve combustions and emission properties (vide infra).

As such an embodiment of the invention is where more than one target molecule is produced as a constituent of a mixture or blend within a single engineered strain by engineering for the accumulation of pools of more than one intermediate. This has been observed to occur in many of the inventors' phytol producing strains where build-up and production of geranylgeraniol is concomitant with that of phytol. Strategies are envisioned for the production of two or more target molecules with larger chemical differences in them (relatively to the minor chemical differences noted between phytol and GG-OH).

Continuing on, another embodiment of the invention is where more than one target molecule is produced as a mixture or blend by co-culture of more than one engineered organism (each producing a distinct target fuel molecule or a distinct set of target molecules). A first iteration of the embodiment is where a co-culture would be for organisms of the same moiety. A second iteration involves the co-culture of multiple moieties in the same vessel.

While the dimensions, species, types of other materials and media described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

The invention claimed is:

1. A method for producing phytol and phytol-related branched C20 alcohols for biofuels using bacteriochlorophyll producing bacteria, the method comprising:
   a. modifying the bacterium's bacteriochlorophyll biosynthesis pathway to increase production of chlorophyll and its anchors which range in length from 5 carbons to 70 carbons; wherein the bacterium's bacteriochlorophyll biosynthesis pathway is modified by inserting and expressing in the bacterium a gene encoding a heterologous plant chlorophyllase and by modifying the organism's genome to no longer express phytoene synthase by deleting a gene coding for the enzyme crtB;
   b. growing the modified bacterium in suitable growth media so as to accumulate biomass; and
   c. harvesting the phytol and phytol-related branched C20 alcohols from the biomass.

2. The method as recited in claim 1 wherein the phytol and phytol-related branched C20 alcohols are molecules selected from the group consisting of phytol, the biosynthetic precursors of phytol, the reduced forms of phytol, and combinations thereof.

3. The method as recited in claim 1 wherein a portion of the phytol and phytol-related branched C20 alcohols are exported from the bacteria into the growth media.

4. The method as recited in claim 1 wherein the step of harvesting the phytol and phytol-related branched C20 alcohols further comprises separating them from the growth media.

5. The method as recited in claim 1 wherein the step of harvesting the phytol and phytol-related branched C20 alcohols further comprises extracting the phytol and phytol-related branched C20 alcohols from storage reserves residing in the bacteria.

6. The method as recited in claim 5 wherein the phytol and phytol-related branched C20 alcohols are stored in the bacteria to the point where the bacteria become buoyant in the growth media, after which the buoyant bacteria are removed from the top of the growth media.

7. The method as recited in claim 5 wherein the bacteria is *R. sphaeriodes* and the step of extracting the phytol and phytol-related branched C20 alcohols from storage reserves further comprises lysing the bacteria by infecting the bacteria with the bacteriophage RS1.

8. The method as recited in claim 1 wherein lipids are by-products.

9. A method for producing phytol, the method comprising:
   a. modifying a *Rhodobacter* organism by inserting and expressing in the organism a gene encoding a heterologous plant chlorophyllase and by modifying the organism's genome to no longer express phytoene synthase by interrupting a gene coding for the enzyme crtB;
   b. growing the organism to accumulate biomass;
   c. removing phytol from the biomass.

10. The method as recited in claim 9 wherein the expressed chlorophyllase severs phytol from chlorophyll.

11. The method as recited in claim 9 wherein the organism is grown in media and the phytol is removed from the media.

12. The method as recited in claim 1 wherein the gene encoding the plant chlorophyllase is from a plant selected from the group consisting of corn, soybean, *Ginkgo biloba*, *Arabidopsis* and *Brassica*.

13. The method as recited in claim 9 wherein the gene encoding the plant chlorophyllase is from a plant selected from the group consisting of corn, soybean, *Ginkgo biloba*, *Arabidopsis* and *Brassica*.

14. The method as recited in claim 1 wherein the bacteria yields phytol ranging between about 5 and 10 percent of the dry weight of the bacterial cells.

15. The method as recited in claim 9 wherein the organism yields phytol ranging between about 5 and 10 percent of the dry weight of the organism's cells.

16. The method of claim 1 wherein the phytol and phytol-related branched C20 alcohols extracted from the biomass are suitable for use as fuel or fuel additive without further refining.

17. The method of claim 9 wherein the phytol extracted from the biomass is suitable for use as fuel or fuel additive without further refining.

18. The method as recited in claim 1 wherein the bacteria yields phytol ranging between about 1 and 2 percent of the dry weight of the bacterial cells.

19. The method as recited in claim 9 wherein the organism yields phytol ranging between about 1 and 2 percent of the dry weight of the organism's cells.

\* \* \* \* \*

SEQUENCE LISTING

<160> NUMBER OF SEQ ID NOS: 22

<210> SEQ ID NO 1
<211> LENGTH: 29
<212> TYPE: DNA
<213> ORGANISM: Rhodobacter sphaeroides

<400> SEQUENCE: 1
gaattcaaaa tgccctcgat ctcgcccgc                                              29

<210> SEQ ID NO 2
<211> LENGTH: 24
<212> TYPE: DNA
<213> ORGANISM: Rhodobacter sphaeroides

<400> SEQUENCE: 2
tcattccgcg gcaagccttt cagc                                                   24

<210> SEQ ID NO 3
<211> LENGTH: 37
<212> TYPE: DNA
<213> ORGANISM: Rhodobacter sphaeroides

<400> SEQUENCE: 3
ggcttgccgc ggaatgaggg gggggaaagc cacgttg                                     37

<210> SEQ ID NO 4
<211> LENGTH: 35
<212> TYPE: DNA
<213> ORGANISM: Rhodobacter sphaeroides

<400> SEQUENCE: 4
gcccagtcca tgttcatccc ccggatccgt cgacc                                       35

<210> SEQ ID NO 5
<211> LENGTH: 27
<212> TYPE: DNA
<213> ORGANISM: Rhodobacter sphaeroides

<400> SEQUENCE: 5
atgaacatgg actgggctct tttcctc                                                27

<210> SEQ ID NO 6
<211> LENGTH: 27
<212> TYPE: DNA
<213> ORGANISM: Rhodobacter sphaeroides

<400> SEQUENCE: 6
gaattcaaat caggcgcggg cttcggg                                                27

<210> SEQ ID NO 7
<211> LENGTH: 18
<212> TYPE: DNA
<213> ORGANISM: Artificial Sequence
<220> FEATURE:
<223> OTHER INFORMATION: Oligos used in PCR reactions to confirm allelic
      exchange of crtB and Km

<400> SEQUENCE: 7 gcaggggca aggggggc                                                           18

<210> SEQ ID NO 8
<211> LENGTH: 22
<212> TYPE: DNA

```
<213> ORGANISM: Artificial Sequence
<220> FEATURE:
<223> OTHER INFORMATION: Oligos used in PCR reactions to confirm allelic
      exchange of crtB and Km

<400> SEQUENCE: 8
gccatcctat ggaactgcct cg                                          22

<210> SEQ ID NO 9
<211> LENGTH: 20
<212> TYPE: DNA
<213> ORGANISM: Artificial Sequence
<220> FEATURE:
<223> OTHER INFORMATION: Oligos used in PCR reactions to confirm allelic
      exchange of crtB and Km

<400> SEQUENCE: 9
ctctggcgca tcgggcttcc                                             20

<210> SEQ ID NO 10
<211> LENGTH: 20
<212> TYPE: DNA
<213> ORGANISM: Artificial Sequence
<220> FEATURE:
<223> OTHER INFORMATION: Oligos used in PCR reactions to confirm allelic
      exchange of crtB and Km

<400> SEQUENCE: 10
cctcctgcag atggggtggg                                             20

<210> SEQ ID NO 11
<211> LENGTH: 55
<212> TYPE: DNA
<213> ORGANISM: Brassica oleracea

<400> SEQUENCE: 11
ctgtactagt ggaggatagt aatgcaaaac tttgcagaat ctcatcaact ttcag       55

<210> SEQ ID NO 12
<211> LENGTH: 43
<212> TYPE: DNA
<213> ORGANISM: Brassica oleracea

<400> SEQUENCE: 12
tgtaagatct tcacagaaaa gagtcaaatt tgatctccac tgg                   43

<210> SEQ ID NO 13
<211> LENGTH: 40
<212> TYPE: DNA
<213> ORGANISM: Brassica oleracea

<400> SEQUENCE: 13
tgtaagatct cagaaaagag tcaaatttga tctccactgg                       40

<210> SEQ ID NO 14
<211> LENGTH: 44
<212> TYPE: DNA
<213> ORGANISM: Brassica oleracea

<400> SEQUENCE: 14
ctgtactagt ggaggatagt aatgaacctc gcgtccgcgg tgcg                  44

<210> SEQ ID NO 15
<211> LENGTH: 45
<212> TYPE: DNA
```

<213> ORGANISM: Brassica oleracea

<400> SEQUENCE: 15
tgtaagatct agctatcgct ttctcatctc caaactccac cacgg                45

<210> SEQ ID NO 16
<211> LENGTH: 48
<212> TYPE: DNA
<213> ORGANISM: Brassica oleracea

<400> SEQUENCE: 16
tgtaagatct ctaagctatc gctttctcat ctccaaactc caccacgg             48

<210> SEQ ID NO 17
<211> LENGTH: 56
<212> TYPE: DNA
<213> ORGANISM: Brassica oleracea

<400> SEQUENCE: 17
ctgtactagt ggaggatagt aatggcggcg atagaggaca gtccaacgtt ttcctc    56

<210> SEQ ID NO 18
<211> LENGTH: 43
<212> TYPE: DNA
<213> ORGANISM: Brassica oleracea

<400> SEQUENCE: 18
tgtaagatct gacgaagata ccagaagctt cttccaactc agg                  43

<210> SEQ ID NO 19
<211> LENGTH: 46
<212> TYPE: DNA
<213> ORGANISM: Brassica oleracea

<400> SEQUENCE: 19
tgtaagatct ctagacgaag ataccagaag cttcttccaa ctcagg               46

<210> SEQ ID NO 20
<211> LENGTH: 48
<212> TYPE: DNA
<213> ORGANISM: Brassica oleracea

<400> SEQUENCE: 20
ctgtactagt ggaggatagt aatggcgggg aaggaggaca gtgagacg             48

<210> SEQ ID NO 21
<211> LENGTH: 43
<212> TYPE: DNA
<213> ORGANISM: Brassica oleracea

<400> SEQUENCE: 21
tgtaagatct gacgagataa ccagaagcct cttccagctc cgg                  43

<210> SEQ ID NO 22
<211> LENGTH: 998
<212> TYPE: DNA
<213> ORGANISM: Brassica oleracea

<400> SEQUENCE: 22
actagtggag gatagtaatg gcggggaagg aggacagtga gacgttttc tcggcggcaa         60 ctcctttggc gtttgagtta ggcagccttc aacaaccgt gatccccgca gacccgtcgg        120
caaccgattt gaccgcacct ccgaagcctg taataatcac ctccccgacc gtcgccggaa       180

```
cttaccccgt cgtcctgttc ttccatggat tctatcttcg taactacttc tactctgatg      240
ttattaacca cgtagcttct catggctaca ttgttgtggc cccgcagctt tgcaagattt      300
tgccgccggg agggcaagtg gaagtggacg atgctggaaa agtgatcaac tggacttcga      360
aaaacctcaa agctcacctc ccgagttcag tgaacgctaa tggcaactac accgcactcg      420
tgggtcatag ccgcggtggt aaaaccgcgt ttgcggttgc gctgggccac gccgcaacac      480
tggacccatc catcaagttt tcggctcttg taggaataga tccggttgca ggaatcagca      540
aatgcatacg caccgatccc gaaatcctga cgtacaaacc ggaatcattc gacctggaca      600
tgccggttgc agtgatcggt acgggtctcg gaccgaagag taacatgctg atgccgccgt      660
gcgcaccggc ggaagtgaac catgaggagt tttatattga gtgcaaggct acgaagggac      720
atttcgtggc tgcggattac ggacatatgg atatgttgga cgataatttg cccggttttg      780
tcgggtttat ggcgggttgc atgtgcaaga acggtaaacg caaaaagagt gagatgagaa      840
gctttgttgg tggaattgtg gttgcgtttc taaagtatag tatatggggt gaaatgtcag      900
agattcgaca gattttgaag gatccttctg tttctccagc gaggcttgat ccttcgccgg      960
agctggaaga ggcttctggt tatctcgtct agagatct                             998
```